(12) United States Patent
Miklatzky et al.

(10) Patent No.: US 10,292,482 B2
(45) Date of Patent: May 21, 2019

(54) HAIR-HOLDER, HAIR-READER COMPRISING THE SAME, AND METHODS FOR OPTICALLY ACQUIRING DATA FROM HAIR

(71) Applicant: COLORIGHT LTD., Rehovot (IL)

(72) Inventors: Efraim Miklatzky, Nevellan (IL); Tal Marcu, Mevaseret Zion (IL)

(73) Assignee: COLORIGHT LTD., Rehovot (IL)

( * ) Notice: Subject to any disclaimer, the term of this patent is extended or adjusted under 35 U.S.C. 154(b) by 161 days.

(21) Appl. No.: 15/399,796

(22) Filed: Jan. 6, 2017

(65) Prior Publication Data
US 2018/0192764 A1 Jul. 12, 2018

(51) Int. Cl.
*A45D 44/00* (2006.01)
*A45D 8/00* (2006.01)
(Continued)

(52) U.S. Cl.
CPC ............ *A45D 44/005* (2013.01); *A45D 8/00* (2013.01); *G01N 21/25* (2013.01); *G01N 21/84* (2013.01);
(Continued)

(58) Field of Classification Search
CPC .. A45D 44/005; A45D 8/00; A45D 2044/007; G01N 21/25; G01N 33/4833; G01N 21/84
(Continued)

(56) References Cited

U.S. PATENT DOCUMENTS 9,205,283 B2 * 12/2015 Miklatzky ............... A45D 19/02
9,844,687 B2 * 12/2017 Landa ..................... A45D 19/02
(Continued)

FOREIGN PATENT DOCUMENTS

DE   10 2007 055 100 B3   12/2008
JP       2000-205959 A      7/2000
(Continued)

OTHER PUBLICATIONS

International Search Report and Written Opinion dated May 23, 2018 in PCT/IB2018/000040, citing documents AA, AB, AC, AD, AO, AP and AQ therein, 15 pages.

*Primary Examiner* — Michael Collins
(74) *Attorney, Agent, or Firm* — Oblon, McClelland, Maier & Neustadt, L.L.P.

(57) ABSTRACT

A system for optically acquiring data from hair comprises a hair-holder including: upper and lower plate assemblies respectively having downward-facing and upward-facing opposing surfaces defining a gap therebetween, the lower plate assembly having a window-void therein, the upper plate assembly further comprising a sideward-facing sample-thickness-regulating surface above the gap; and an alignment-wall mechanically coupled to both plate assemblies and having a side-facing alignment surface within gap or sideward-facing into the gap, the alignment surface being straight along a longitudinal direction parallel to both of the opposing surfaces, the hair-holder being configured so that: when an externally-tensioned sample of hair is loaded onto the hair-holder by laterally moving the sample towards the alignment surface, a presence of the sideward-facing sample-thickness-regulating surface regulates an amount of hair permitted to enter the gap, thereby regulating a thickness of hair above the window-void to at least 0.5 mm and at most 2 mm, and after the loading and after release of the external tension, static friction applied by the side-facing alignment surface upon shafts of the hair sample maintain alignment of hair above the window-void.

17 Claims, 25 Drawing Sheets

(51) Int. Cl.
  *G01N 21/25* (2006.01)
  *G01N 33/483* (2006.01)
  *G01N 21/84* (2006.01)

(52) U.S. Cl.
  CPC ... *G01N 33/4833* (2013.01); *A45D 2044/007* (2013.01)

(58) Field of Classification Search
  USPC .................................................. 700/231–244
  See application file for complete search history.

(56) References Cited

U.S. PATENT DOCUMENTS

| | | |
|---|---|---|
| 10,012,588 B2 * | 7/2018 | Miklatzky ............... G01J 3/463 |
| 10,046,183 B2 * | 8/2018 | Landa .................. B65D 1/0223 |
| 2008/0260243 A1 | 10/2008 | Occelli |
| 2012/0320191 A1 | 12/2012 | Meschkat et al. |
| 2014/0118521 A1 | 5/2014 | Conti et al. |
| 2016/0011051 A1 | 1/2016 | Conti et al. |

FOREIGN PATENT DOCUMENTS

| | | |
|---|---|---|
| WO | WO 2006/134429 A2 | 12/2006 |
| WO | WO 2006/134429 A3 | 12/2006 |

* cited by examiner

HAIR-HOLDER, HAIR-READER COMPRISING THE SAME, AND METHODS FOR OPTICALLY ACQUIRING DATA FROM HAIR

BACKGROUND

The following issued patents and patent publications provide potentially relevant background material, and are all incorporated by reference in their entirety: U.S. Pat. Nos. 4,643,313, 5,205,837, 5,660,342, 5,754,283, 5,851,181, 5,990,058, 6,096,359, 6,170,980, 6,248,749, 6,362,885, 6,529,446, 6,547,833, 6,613,311, 6,707,929, 6,764,523, 6,790,240, 6,818,022, 6,984,377, 7,110,117, 7,204,856, 7,304,739, 7,458,992, 7,463,356, 7,508,508, 7,523,018, 7,708,021, US 20010002025, US 20020010556, US 20020157191, US 20020194684, US 20030028978, US 20040000015, US 20040013616, US 20050015895, US 20050019398, US 20050039271, US 20050165705, US 20050177032, US 20050244343, US 20060149151, US 20060195300, US 20070159290, US 20070265867, US 20080013077, US 20080068604, US 20080256724, US 20090119852, US 20110038818, DE 10260880, DE 2006008149, DE 3609962, DE 4205112, EP 0590538, EP 1817976, EP 2081668, EP 2193781, FR 2402446, FR 2532174, FR 2901131, JP 2000116622, JP 2004198398, JP 2004212088, JP 2007212140, JP 2008285429, KR100802645, KR20040076861, WO 0145647, WO 02083282, WO 03012728, WO 03074015, WO 04101689, WO 11003554, WO 2004058202, WO 2004082650, WO 2004101689, WO 2008046518, WO 2009121643, WO 2009152033, WO 2010004565, WO 2010060601, WO 2010100231, WO 2012032671, WO/2015/166340, WO/2015/044944 and WO/2015/166403.

SUMMARY OF EMBODIMENTS

Embodiments of the invention relate to a hair-holder device comprising upper and lower plate assemblies and adapted for use with an optical measuring instrument (e.g. spectrometer or camera). In some embodiments, after a hair-sample is loaded into the hair-holder device, the hair-shafts of the sample are illuminated via a window-void of the lower-plate assembly. Light reflected from and/or transmitted by and/or deflected by the illuminated hair is collected by the optical measuring instrument.

In different embodiments, the hair-holder device is designed (i) to minimize the effort required by a user (e.g. hair-dresser) who wishes to ensure that a very specific thickness of hair (i.e. between 0.5 mm and 2 mm) is disposed over a window-void of the lower-plate assembly; and (ii) to maintain alignment of hair-shafts that are disposed over the window-void, without requiring external tensioning for this purpose. In some embodiments, static friction applied by a side-facing alignment surface (discussed below) serves this purpose, and obviates the need for the user to maintain the sample of hair under external tension during imaging and/or measurement of spectrum(a).

Data optically acquired by the optical measuring instrument may be used to predict a result of a hypothetical hair-treatment protocol and/or to compute a hair-treatment predicted to transform the hair to a target color-state.

In addition to the hair-holder device, systems including the hair-holder device and methods of using the hair-holder device are disclosed herein.

Some embodiments relate to a system for optically acquiring data from hair, the system comprising: a hair-holder including: upper and lower plate assemblies defining a gap therebetween, the lower plate assembly having a window-void therein, the upper plate assembly further comprising a sideward-facing sample-thickness-regulating surface above the gap; and an alignment-wall mechanically coupled to both plate assemblies and having a side-facing alignment surface within gap or sideward-facing into the gap, the alignment surface being straight along a longitudinal direction parallel to both of the opposing surfaces.

In some embodiments, the hair-holder is configured so that: when an externally-tensioned sample of hair is loaded onto the hair-holder by laterally moving the sample towards the alignment surface, a presence of the sideward-facing sample-thickness-regulating surface regulates an amount of hair permitted to enter the gap, thereby regulating a thickness of hair above the window-void to a fixed value of at least 0.5 mm and at most 2 mm.

In some embodiments, after the loading and after release of the external tension, static friction applied by the side-facing alignment surface upon shafts of the hair sample maintain alignment of hair above the window-void.

A system for optically acquiring data from hair comprises a hair-holder including: upper and lower plate assemblies respectively having downward-facing and upward-facing opposing surfaces defining a gap therebetween, the lower plate assembly having a window-void therein, the upper plate assembly further comprising a sideward-facing sample-thickness-regulating surface above the gap; and an alignment-wall mechanically coupled to both plate assemblies and having a side-facing alignment surface within gap or sideward-facing into the gap, the alignment surface being straight along a longitudinal direction parallel to both of the opposing surfaces, the hair-holder being configured so that: when an externally-tensioned sample of hair is loaded onto the hair-holder by laterally moving the sample towards the alignment surface, a presence of the sideward-facing sample-thickness-regulating surface regulates an amount of hair permitted to enter the gap, thereby regulating a thickness of hair above the window-void to at least 0.5 mm and at most 2 mm (in some embodiments, at most 1 cm or at most 5 mm or at most 3 mm or at most 2 mm or at most 1.5 mm or at most 1 mm); and after the loading and after release of the external tension, static friction applied by the side-facing alignment surface upon shafts of the hair sample maintain alignment of hair above the window-void.

In some embodiments, further comprising at least one light-source configured to illuminate the aligned shafts via the window-void.

In some embodiments, the light-source is selected from the group consisting of an LED, a halogen source and a high intensity discharge source.

In some embodiments, the light-source emits light at a wavelength of at least 750 nm.

In some embodiments, further comprising a spectrometer for measuring at least one spectrum of the aligned shafts upon receiving, via the window-void, light reflected by or transmitted by or deflected by the aligned shafts.

In some embodiments, further comprising a digital camera for digitally acquiring a digital image of the aligned shafts upon receiving, via the window-void, from light reflected by or transmitted by or deflected by the aligned shafts.

In some embodiments, further comprising a hair-coloring prediction engine for predicting from the digital image and/or from the spectrum(a), a result of a hypothetical hair-coloring treatment upon hair of the sample.

In some embodiments, further comprising an automatic dispenser having a plurality of compartments, each compartment storing a different respective hair-coloring material, the dispenser configured to produce a mixture of ingredients for a customized hair-coloring treatment by automatically dispensing material from each of the compartments at relative quantities computed in accordance with the digital image or the spectrum(a) or the prediction of the hair-coloring treatment.

In some embodiments, where the upper plate assembly has a window-void therein, at least a portion of the window-void of the upper plate assembly being directly above the window-void of the lower plate assembly.

A method for optically acquiring data from hair, the system comprising: providing a hair-holder including: upper and lower plate assemblies respectively having downward-facing and upward-facing opposing surfaces defining a fixed gap therebetween defining a gap therebetween, the lower plate assembly having a window-void therein, the upper plate assembly further comprising a sideward-facing sample-thickness-regulating surface above the gap; and an alignment-wall mechanically coupled to both plate assemblies and having a side-facing alignment surface within gap or sideward-facing into the gap, the alignment surface being straight along a longitudinal direction parallel to both of the opposing surfaces; receiving an externally-tensioned sample of hair onto the hair-holder such that the externally-tensioned sample of hair is laterally moved towards the alignment surface and a presence of the sideward-facing sample-thickness-regulating surface regulates an amount of hair permitted to enter the gap, thereby regulating a thickness of hair above the window-void to a fixed value of at least 0.5 mm and at most 2 mm; and after the loading and after release of the external tension, the side-facing alignment surface applies static friction upon shafts of the hair sample so as to maintain alignment of hair above the window-void.

In some embodiments, further comprising illuminate the aligned shafts via the window-void.

In some embodiments, the light-source is selected from the group consisting of an LED, a halogen source and a high intensity discharge source.

In some embodiments, the light-source emits light at a wavelength of at least 750 nm.

In some embodiments, further comprising receiving, via the window-void and by a spectrometer, light that is reflected by or transmitted by or deflected by the aligned shafts, so as to measure at least one spectrum of the aligned shafts.

In some embodiments, further comprising receiving, via the window-void and by a digital camera, light that is reflected by or transmitted by or deflected by the aligned shafts, so as to digitally acquire an image of the aligned shafts.

In some embodiments, further comprising electronically operating a hair-coloring prediction engine to predict from the digital image and/or from the spectrum(a), a result of a hypothetical hair-coloring treatment upon hair of the sample.

In some embodiments, further comprising: providing an automatic dispenser having a plurality of compartments, each compartment storing a different respective hair-coloring material; and operating the automatic dispenser to produce a mixture of ingredients for a customized hair-coloring treatment by automatically and electronically dispensing material from each of the compartments at relative quantities computed in accordance with the digital image or the spectrum(a) or the prediction of the hair-coloring treatment.

A method for optically acquiring data from hair, the method comprising: assembling a hair-holder by engaging upper and lower plate assemblies to each other so that they are parallel to each other at a separation distance of at most 5 mm so that: a downward-facing surface of the upper plate faces an upward-facing surface of the lower plate as opposing and parallel surfaces that both face into the gap; a sideward-facing sample-thickness-regulating surface of the upper plate assembly is disposed above the gap; an alignment-wall is mechanically coupled to both plate assemblies and having a side-facing alignment surface within gap or sideward-facing into the gap, the alignment surface being straight along a longitudinal direction parallel to both of the opposing surfaces; receiving an externally-tensioned sample of hair onto the hair-holder such that the externally-tensioned sample of hair is laterally moved towards the alignment surface and a presence of the sideward-facing sample-thickness-regulating surface regulates an amount of hair permitted to enter the gap, thereby regulating a thickness of hair above the window-void to a fixed value of at least 0.5 mm and at most 2 mm; and after the loading and after release of the external tension, the side-facing alignment surface applies static friction upon shafts of the hair sample so as to maintain alignment of hair above the window-void.

In some embodiments, the upper and lower plate assemblies are engaged to each other by rotating one relative to the other.

In some embodiments, the upper and lower plate assemblies are engaged to each other by rotating one relative to the other so that before rotation an angle between a the downward-facing surface of the upper plate and the upward-facing surface of the lower plate as opposing is at least 20 degrees, and after rotation they are parallel to each other.

In some embodiments, the externally tensioned sample of hair is root-region-external hair that is external to the hair-root-region.

In some embodiments, further comprising illuminating the aligned hair shafts of the root-region-external hair of the hair-holder, and receiving light reflected by or deflected by or transmitted by the aligned hair shafts into a spectrometer or digital camera to measure a spectrum or acquire a digital image.

In some embodiments, further comprising: disassembling the hair-holder by disengaging the upper and lower plate assemblies from each other; illuminating hair roots of the hair of the sample via the window void of the lower plate, and receiving light reflected by or deflected by or transmitted by the hair roots into a spectrometer or digital camera to measure a spectrum or acquire a digital image.

In some embodiments, further comprising: before the assembling of the hair-holder, illuminating hair roots of the hair of the sample via the window void of the lower plate, and receiving light reflected by or deflected by or transmitted by the hair roots into a spectrometer or digital camera to measure a spectrum or acquire a digital image.

A method for optically acquiring data from hair, the method comprising: a. providing a hair-holder comprising: i. upper and lower plate assemblies respectively having downward-facing and upward-facing opposing surfaces defining a fixed gap therebetween, a height of the fixed-gap ranging between at least 300 microns and at most 1 cm, the upper plate assembly further comprising a sideward-facing sample-thickness-regulating surface above the fixed-gap; ii. an alignment-wall directly or indirectly rigidly attached to both plate assemblies, the alignment-wall having a side-facing alignment surface within gap or sideways-facing into the gap, the alignment surface being straight along a longitudinal direction parallel to both of the opposing surfaces; ii. a window-void coplanar and/or within the upward-facing surface; b. loading an externally-tensioned sample of hair onto the hair-holder by laterally moving shafts of the sample towards the alignment surface so that: during loading, a presence of the sideward-facing sample-thickness-regulating surface on opposite longitudinal-sides of the window-void regulates an amount of hair permitted to enter the gap so as to regulate a thickness of hair above the window-void to a fixed value of at least 300 microns and at most 1 cm; and after loading and after release of the external tension, static friction applied by the side-facing alignment surface upon shafts of the hair sample maintain alignment of hair above the window-void; c. subjecting hair of the sample to a spectral and/or colorimeteric measurement by illuminating the hair via the window-void.

In some embodiments, the fixed value of the thickness of hair above the window-void is at least 400 microns.

In some embodiments, the fixed value of the thickness of hair above the window-void is at most 5 mm, or at most 3 mm or at most 2 mm.

In some embodiments, a reflection spectrum is generated from light reflected by the illuminated hair.

DETAILED DESCRIPTION OF EMBODIMENTS

Figure 1A:
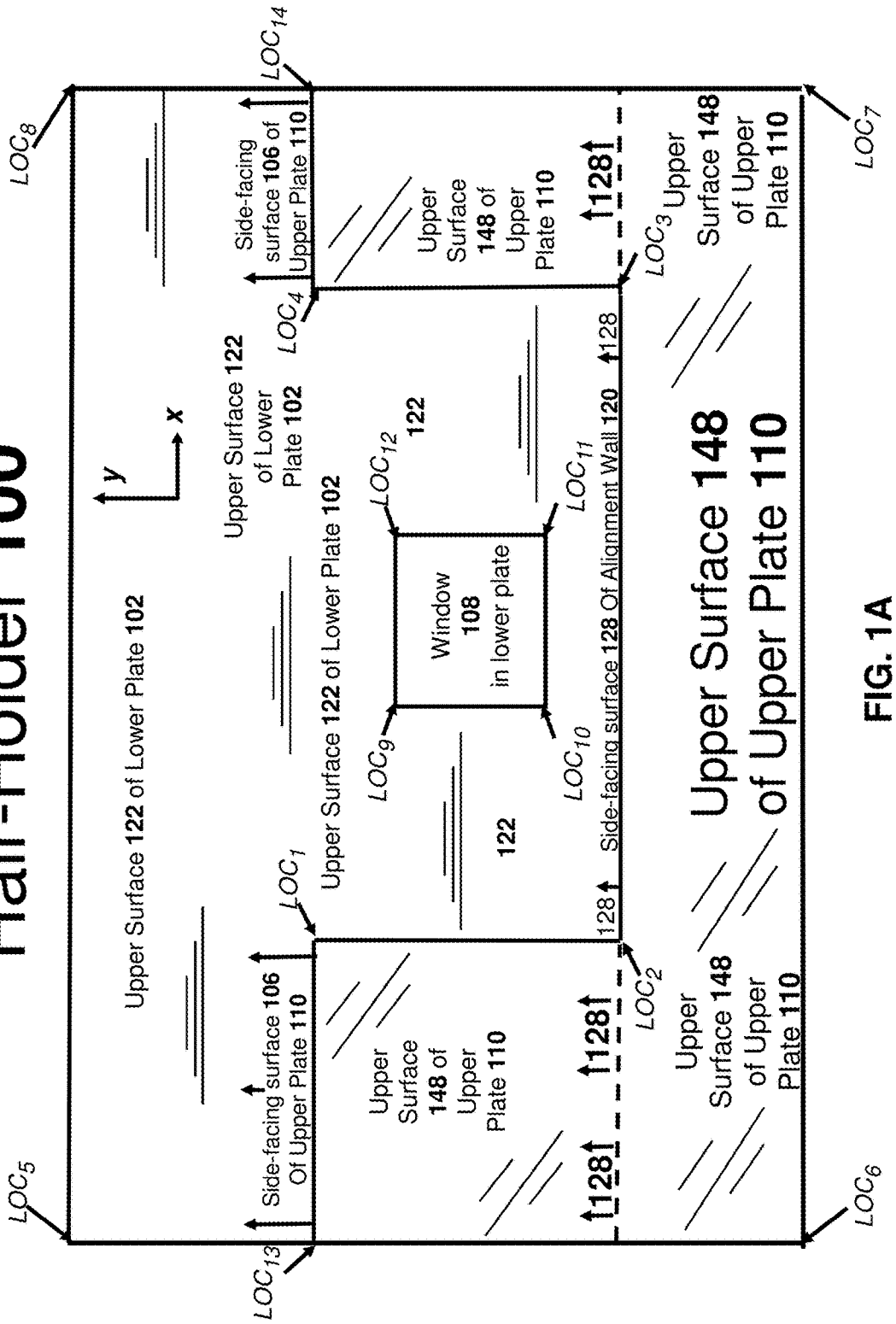
FIGS. 1A-1B, 2A-2E, 3A-3C, 4A-4C, 5A-5B, 6A-6B, 7A-7B, 8 and 11 show various views of a presently-disclosed hair-holder.

The claims below will be better understood by referring to the present detailed description of example embodiments with reference to the figures. The description, embodiments and figures are not to be taken as limiting the scope of the claims. It should be understood that not every feature of the presently disclosed methods and apparatuses is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to'), rather than the mandatory sense (i.e. meaning "must").

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Embodiments of the invention relate to a hair-holder device comprising upper and lower plate assemblies and adapted for use with an optical measuring instrument (e.g. spectrometer or camera). In some embodiments, after a hair-sample loaded into the hair-holder device, the hair-shafts of the sample are illuminated via a window-void of the lower-plate assembly and light reflected from and/or transmitted by and/or deflected by the illuminated hair is collected by the optical measuring instrument.

In different embodiments, the hair-holder device is designed (i) to minimize the effort required by a user (e.g. hair-dresser) who wishes to ensure that a very specific thickness of hair (i.e. between 0.5 mm and 2 mm) is disposed over a window-void of the lower-plate assembly; and (ii) to maintain alignment of hair-shafts that are disposed over the window-void, without requiring external tensioning for this purpose. In some embodiments, static friction applied by a side-facing alignment surface (discussed below) serves this purpose, and obviates the need for the user to maintain the sample of hair under external tension during imaging and/or measurement of spectrum(a).

Experiments indicate that when acquiring spectral or colorimetric data of a sample of hair, a certain thickness may be required in order to obtain results that are not dependent upon the sample thickness—the exact thickness required may depend upon the color or other property(ies) of the hair. For example, in some experiments, a minimum sample thickness of about 400µ is required to achieve a situation where spectral measurements are independent of sample thickness.

Furthermore, it is desired measure aligned hair-shafts. Not wishing to be bound by theory, aligned hair shafts are preferred since, due to hair anisotropy, the hair color appearance may depend upon the direction of the hair shafts relative to an illumination direction of incident light and/or a reflection direction (or transmission direction) of reflected or transmitted light.

Embodiments of the present invention relate to hair-reading system and method for acquiring spectral or colorimetric data from a sample of hair. The sample is loaded into a hair-holder 100 comprising a window-void 108, and an alignment wall for maintaining alignment of shafts of the hair-sample above the window-void. In some embodiments, the geometry of the hair-holder regulates a thickness of the hair-sample that is permitted to locate above the window-void. In different embodiments, the thickness may be at least 300µ or at least 400µ or at least 500µ or at least 600µ of hair and/or at most 1 cm at 5 mm or at most 3 mm or at most 2 mm or at most 1.5 mm or at most 1 mm.

As noted above, the hair-holder 110 comprises an alignment wall 120 for maintaining alignment of shafts of the hair-sample above the window-void 108. In some embodiments, as a result of the mechanical properties of the hair-holder, it is not necessary for a user to maintain the hair sample under external tension for the hair-shafts to stay aligned over the window-void 108—instead, static friction applied by a surface(s) of the hair-holder and the hair-shafts may suffice to maintain hair shaft alignment.

After loading, the sample of hair is illuminated via the window-void 108. Spectral or colorimeteric data is acquired from light that is scattered and/or deflected and/or reflected from the illuminated hair. In some embodiments, the spectral or colorimeteric data is analyzed in order to (i) predict the outcome of a hypothetical hair-coloring treatment as applied to the hair and/or (ii) calculate a customized hair-coloring treatment for the hair.

A 'window void' in a plate assembly is an opening in the plate assembly via which light passes. In contrast to a 'window' which is a transparent object via which light may pass, the 'window void' is empty space. In different embodiments, a window-void 108 may be preferred to a transparent window since the latter might be susceptible to accumulation of dirt on the transparent surface.

In other embodiments, instead of a 'window void' is mentioned, a transparent window (e.g. having any geometric feature of a window-void described herein) may be employed.

Some embodiments of the present invention relate to hair-reading system comprising: (A) a spectrometer or colorimeter 200 for subjecting a hair sample to a spectral or colorimeter measurement and (B) the aforementioned hair-holder 100.

Figure 1B:
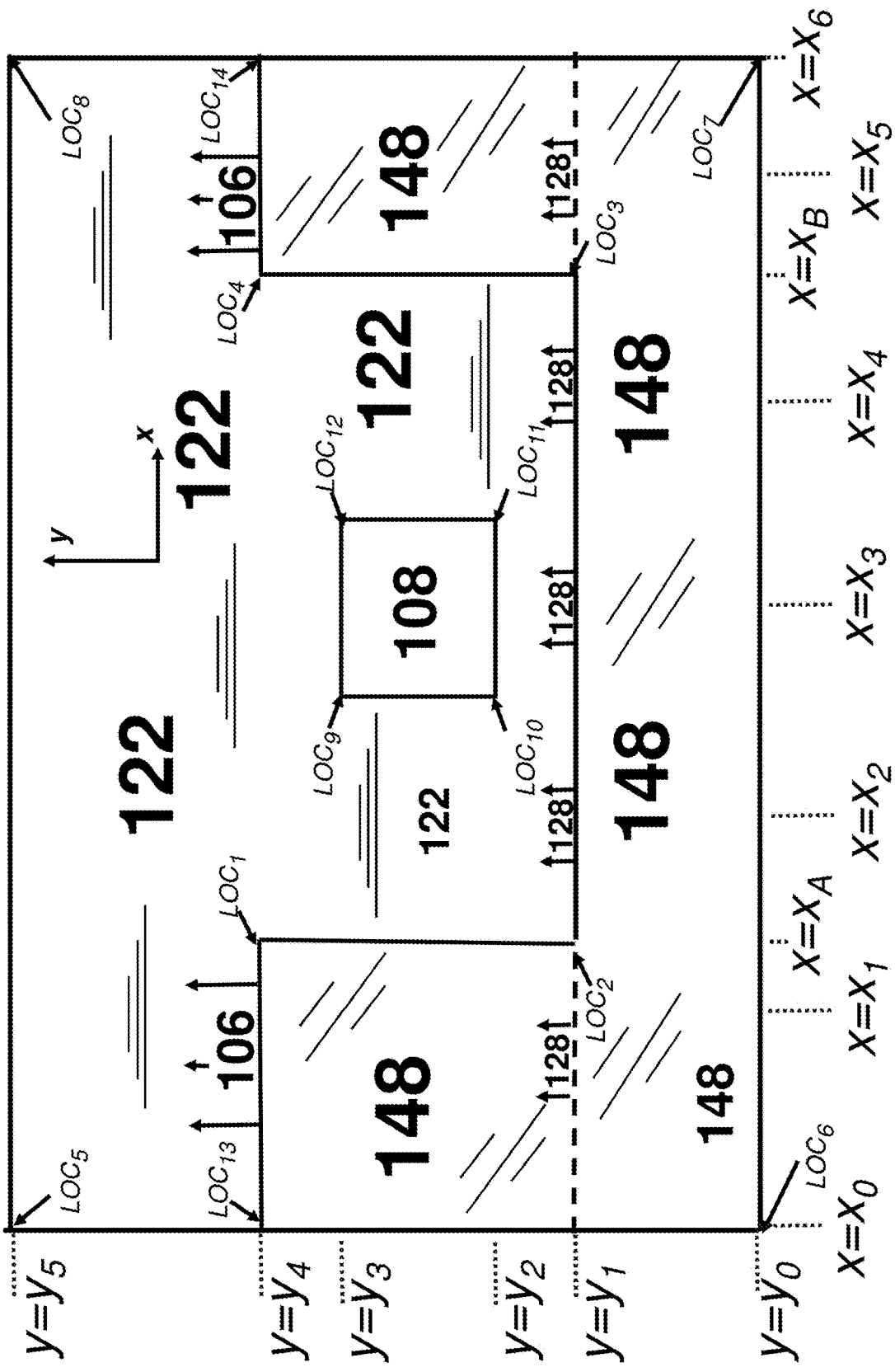

FIGS. 1A-1B illustrates a top view of the hair-holder 100, according to one example. FIGS. 2A-2E illustrates cross-section/side view of the hair-holding devices respectively at positions $x=x_1$, $x=x_2$, $x=x_3$, $x=x_4$, and $x=x_5$.

Some embodiments relate to a system for optically acquiring data from hair, the system comprising: a hair-holder 100 including: upper 110 and lower 102 plate assemblies respectively having downward-facing 154 and upward-facing 122 opposing surfaces defining a gap 158 therebetween, the lower plate assembly 102 having a window-void 108 therein, the upper plate 110 assembly further comprising a sideward-facing sample-thickness-regulating surface 106 above the gap 158; and an alignment-wall 120 mechanically coupled to both plate assemblies and having a side-facing alignment surface 128 (i.e. that is within gap 158 or sideward-facing into the gap 158), the alignment surface 128 being straight along a longitudinal direction parallel to both 154, 122 of the opposing surfaces, the hair-holder being configured so that: when an externally-tensioned sample of hair is loaded onto the hair-holder by laterally moving the sample towards the alignment surface 128, a presence of the sideward-facing sample-thickness-regulating surface 106 regulates an amount of hair permitted to enter the gap 158, thereby regulating a thickness of hair above the window-void 108 to at least 0.5 mm and at most 2 mm; and after the loading and after release of the external tension, static friction applied by the side-facing alignment surface 128 upon shafts of the hair sample maintain alignment of hair above the window-void 108.

Figure 8:
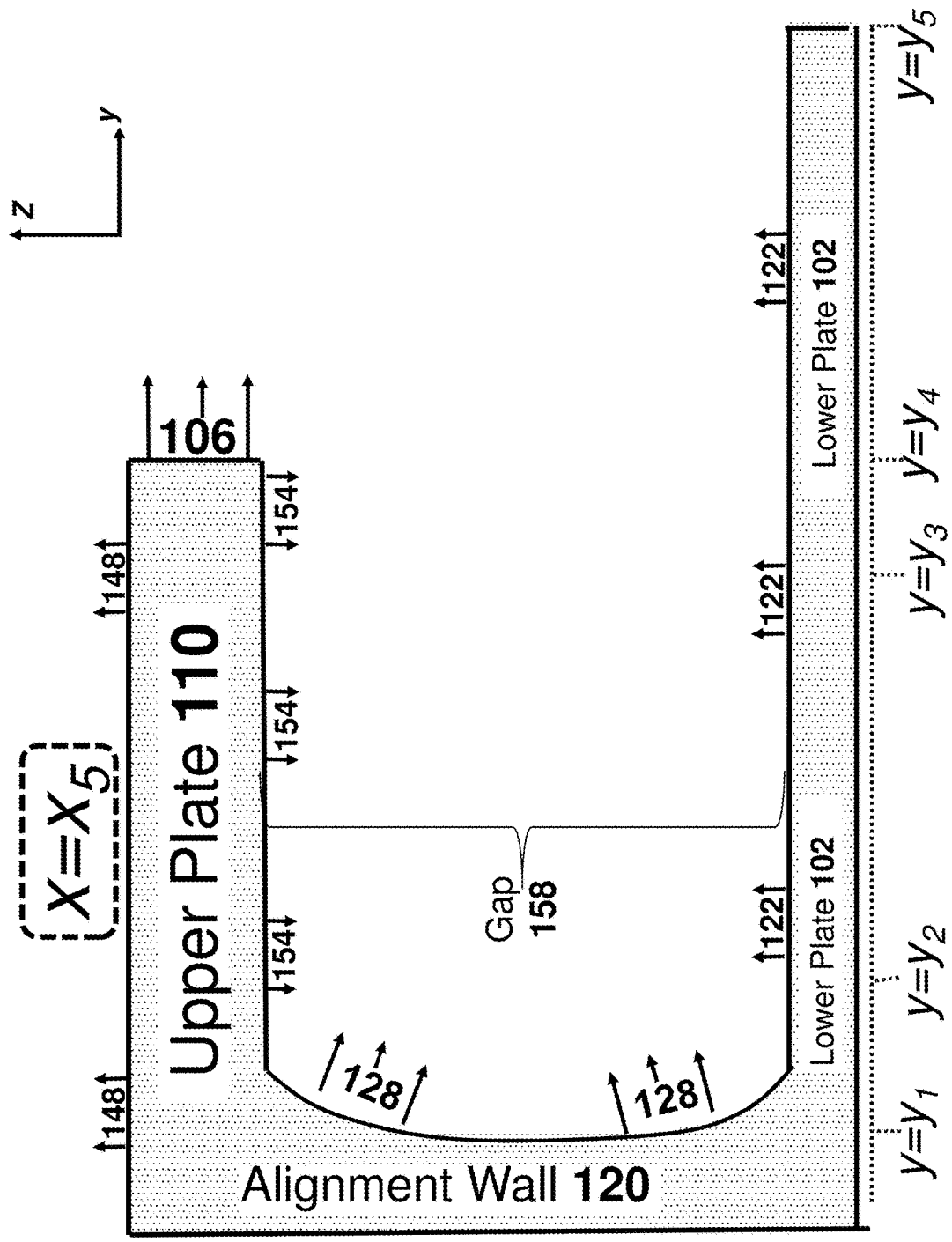

In the examples of FIGS. 1A-1B and 2A-2E the hair-holder 100 comprises (i) upper plate 110 and lower 102 plates (e.g. parallel to each other) defining a gap 158 therebetween and (ii) an alignment wall 120 in gap 158 or facing into the gap 158—a side-facing surface 128 of alignment wall 120 is visible in FIGS. 1A-1B and 2A-2B. As will be discussed below, the function of alignment wall 120 is to maintain alignment of hair shafts within gap 158—e.g. by static friction applied by alignment wall 120. Towards this end and as illustrated in FIGS. 1A-1B, alignment wall 120 may be straight along the x direction. In the example of FIG. 8 the side-facing surface 128 is curved in a 'gap direction along the gap (i.e. the z direction) but is straight in a longitudinal direction (i.e. in the x direction)

In some embodiments, upper 110 and lower 102 plates are rigidly attached to each other to maintain a size of gap 158 characterized by a 'gap distance' to a fixed value. The term 'fixed value' refers to being held fixed in time—however, the gap distance may fluctuate as a function of x or y. The size of gap 158 (i.e. distance between opposing surfaces 154 and 122)) may be fixed in multiple locations between the upper 110 and 102 plates—e.g. at a first and second locations on opposite sides (i.e. in the x direction of window 108. The gap distance may, in different embodiments, be at least 300 microns or at least 400 microns or at least 500 microns and/or at most 1 cm or at most 5 mm or at most 2 mm or at most 1.5 mm or at most 1 mm.

When upper 110 and lower 102 plates are 'rigidly' attached to each other, they may be directly or indirectly attached to each other—in some embodiments, upper 110 and lower 102 plates are rigidly attached to each via alignment wall 120, though this is not a requirement.

Illustrated in FIGS. 1A-1B are the 14 locations $LOC_1$-$LOC_{14}$ in the x-y plane, where "LOC" is an abbreviation for 'location.' A line segment between location $LOC_i$ and location $LOC_j$ (where i and j are positive integers) is denoted by $\overline{Loc_i Loc_j}$.

As illustrated in non-limiting example of the figures, (i) lower plate 102 is larger than upper plate 110; and (ii) the lower plate 102 is rectangular in shape—the borders of lower plate 102 are defined by the following four line-segments in the x-y plane (in counter-clockwise order): (i) $\overline{Loc_5 Loc_6}$, (ii) $\overline{Loc_6 Loc_7}$, (iii) $\overline{Loc_7 Loc_8}$ and (iv) $\overline{Loc_8 Loc_9}$. In contrast, because the outer borders of upper plate 110 have a more complex shape, eight line-segments are required to define the shape of the outer borders of upper plate 110 (in counter-clockwise order): (i) $\overline{Loc_{13} Loc_6}$ (ii) $\overline{Loc_6 Loc_7}$, (iii) $\overline{Loc_7 Loc_{14}}$; (iv) $\overline{Loc_{14} Loc_4}$; (v) $\overline{Loc_4 Loc_3}$; (vi) $\overline{Loc_3 Loc_2}$; (vii) $\overline{Loc_2 Loc_1}$ and (viii) $\overline{Loc_1 Loc_{13}}$.

In the non-limiting example hair-holder illustrated in the figures, locations within the shape defined by the aforementioned eight line-segments, upper plate 110 is present—thus, from a top view, upper surface 148 of upper plate 110 is visible and lower plate 104 (and an upper surface 122) thereof is occluded at these locations. In contrast, in locations in the rectangular-shaped region of space defined by $y_4 < y < y_5$ (alternatively, defined by the four locations $LOC_5$, $LOC_{13}$, $LOC_{14}$, and $LOC_8$) upper plate 110 is absent—as such, in these locations from a top view upper surface 122 of lower plate 104 is visible. Similarly, in locations in the rectangular-shaped region of space where the following two inequalities are simultaneously true (i) $y_1 < y < y_4$ and (ii) $x_A < x < x_B$ (alternatively, defined by the four locations $LOC_{51} LOC_2$, $LOC_3$, and $LOC_4$) upper plate 110 is absent as well—as such, in these locations as well from a top view upper surface 122 of lower plate 104 is visible.

In some embodiments, there is a window 108 within lower plate as well—e.g. characterized by a void in lower plate 102.

Upper plate 110 has upper 148 and lower 154 surfaces facing in opposite directions. Because FIGS. 1A-1B illustrates a top view, only upper surface 148 is visible in FIGS. 1A-1B—lower surface 154 of upper plate 110 is not visible. In addition, as discussed above, upper surface 122 of lower plate 102 is visible in FIGS. 1A-1B and 2A-2E.

As noted above, FIGS. 2A-2E are side views of cross sections of the hair-holder at positions $x=x_1$, $x=x_2$, $x=x_3$, $x=x_4$, and $x=x_5$. As shown in FIGS. 2A-2E, the following surfaces 'face towards' gap 158: (i) upward-facing lower surface 154 of upper plate 110; (ii) downward-facing upper surface 122 of lower plate 102, and (iii) side-facing surface 128 of alignment-wall 120.

The terms 'upward,' 'downward,' 'upper,' 'lower,' 'above,' 'below,' 'sideward' and 'sideways' are reference terms and are not intended as limiting—they refer to the situation where the hair-holder 100 is a whole is in the particular orientation where the lower plate 102 is in a horizontal orientation and below upper plate 110. It is appreciated that hair-holder 100 is not required to be used in this orientation.

Figure 4A:
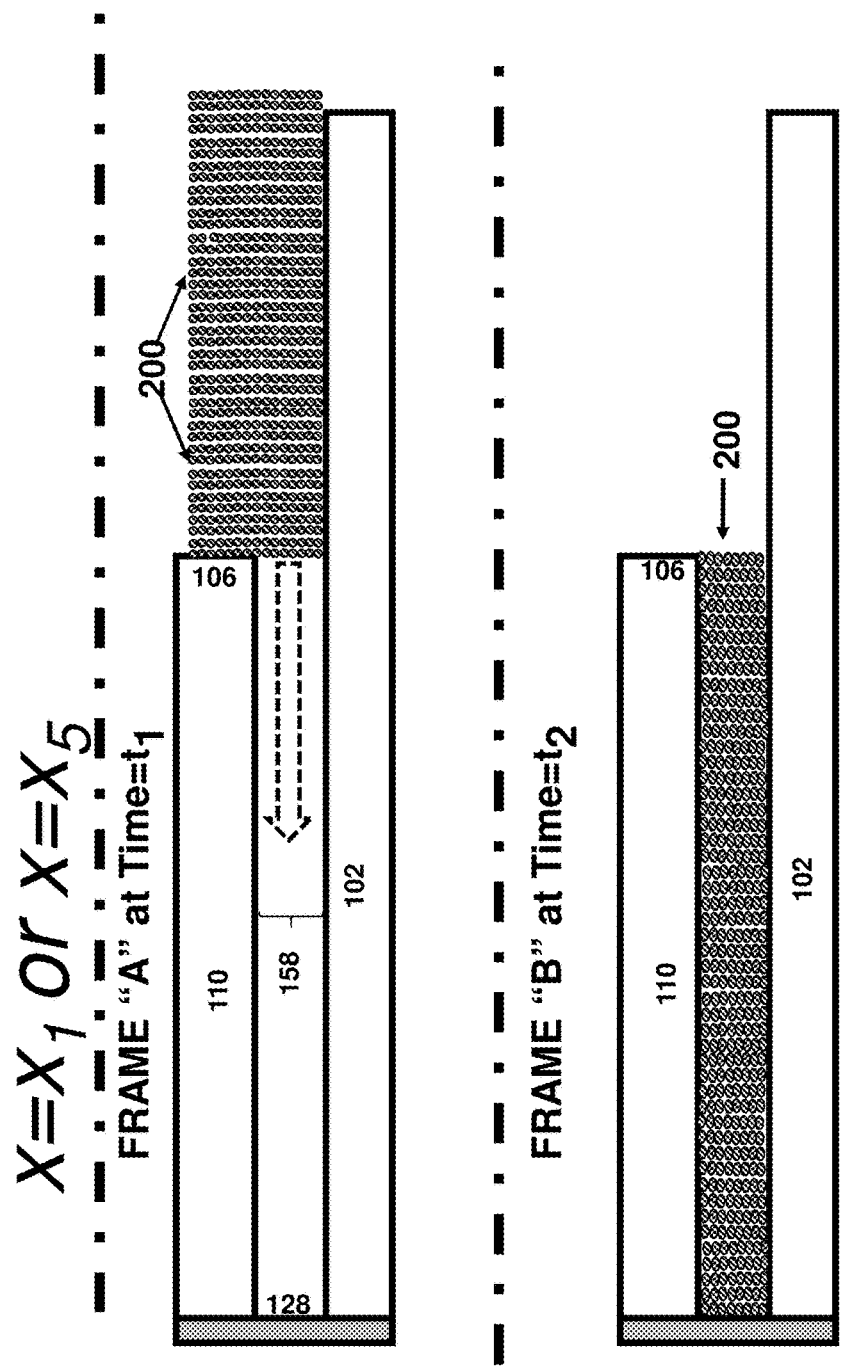
Figure 4B:
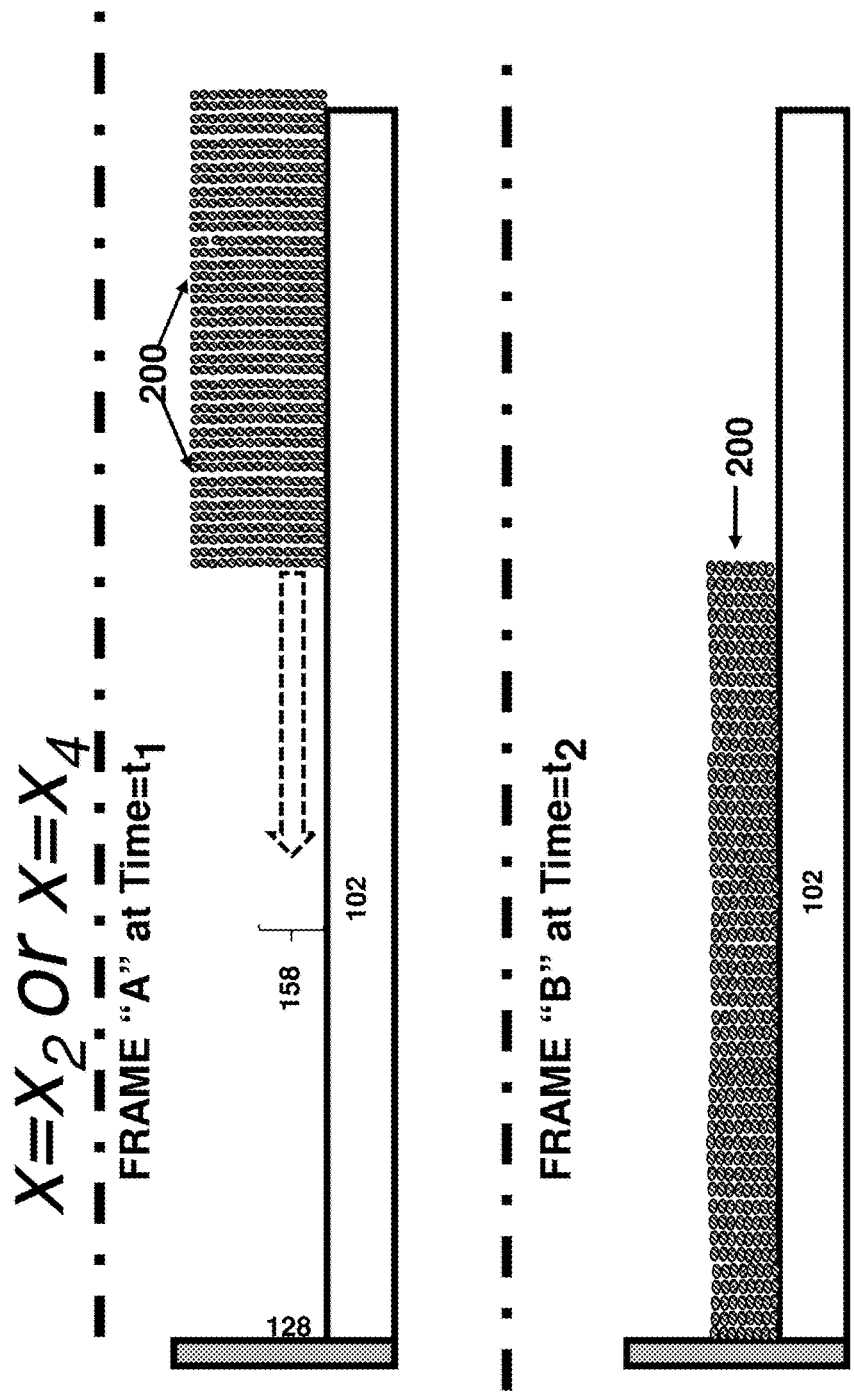
Figure 4C:
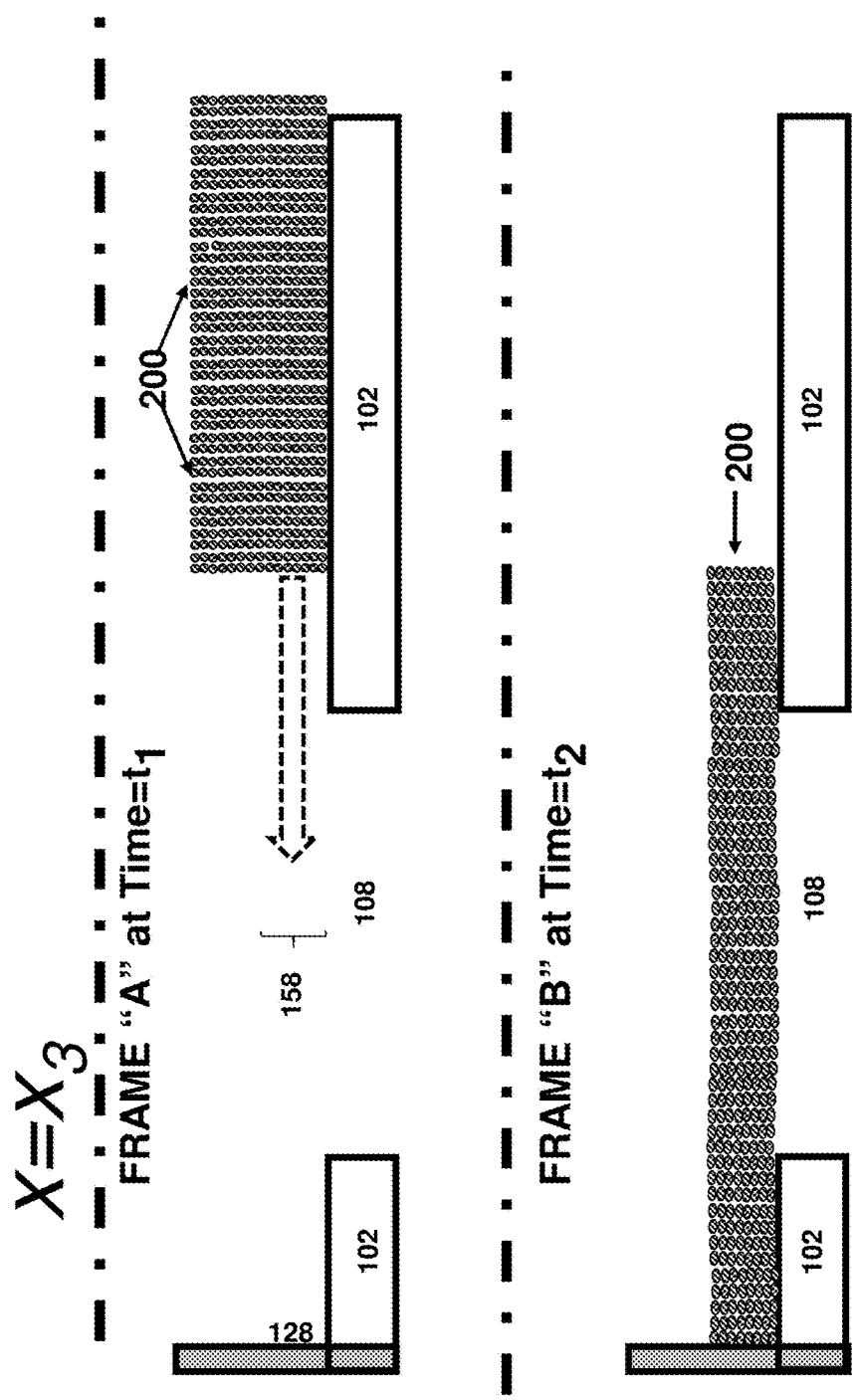

As discussed below, the hair-holder is used when a sample of hair is aligned in a given direction along an alignment-wall, and a side-facing alignment surface thereof maintains alignment. This direction is referred to as the 'longitudinal direction' and it is parallel to both upper surface 122 of lower plate 104 and to lower surface 154 of upper plate 110. The 'lateral direction' is (i) also parallel to both upper surface 122 of lower plate 104 and to lower surface 154 of upper plate 110; and (ii) is perpendicular to the 'longitudinal direction.' As shown in FIGS. 4A-4C, the hair-holder is loaded by movement of hair (e.g. under external tension to maintain shafts aligned with each other) in the 'lateral' direction.

Figure 2A:
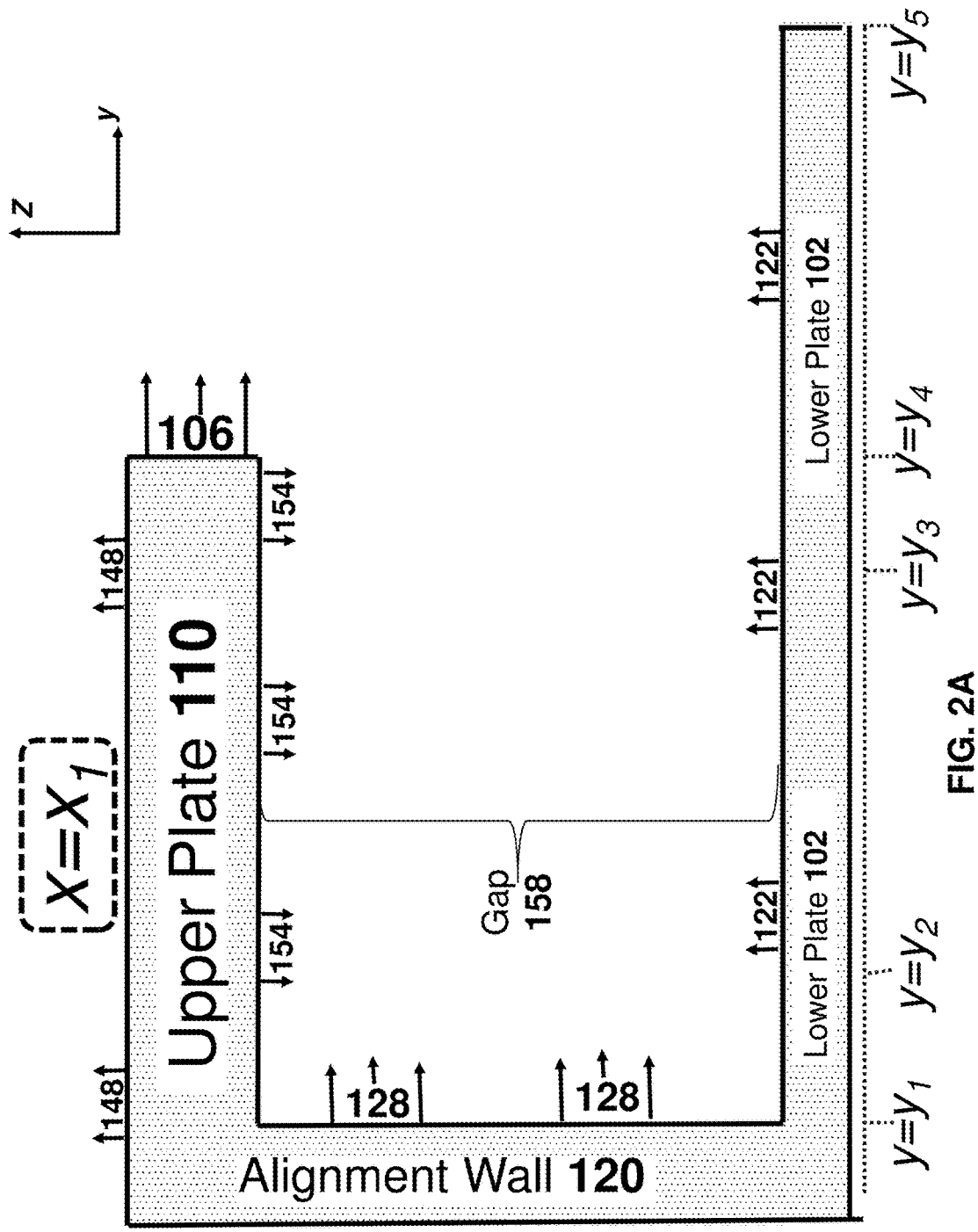
Figure 2B:
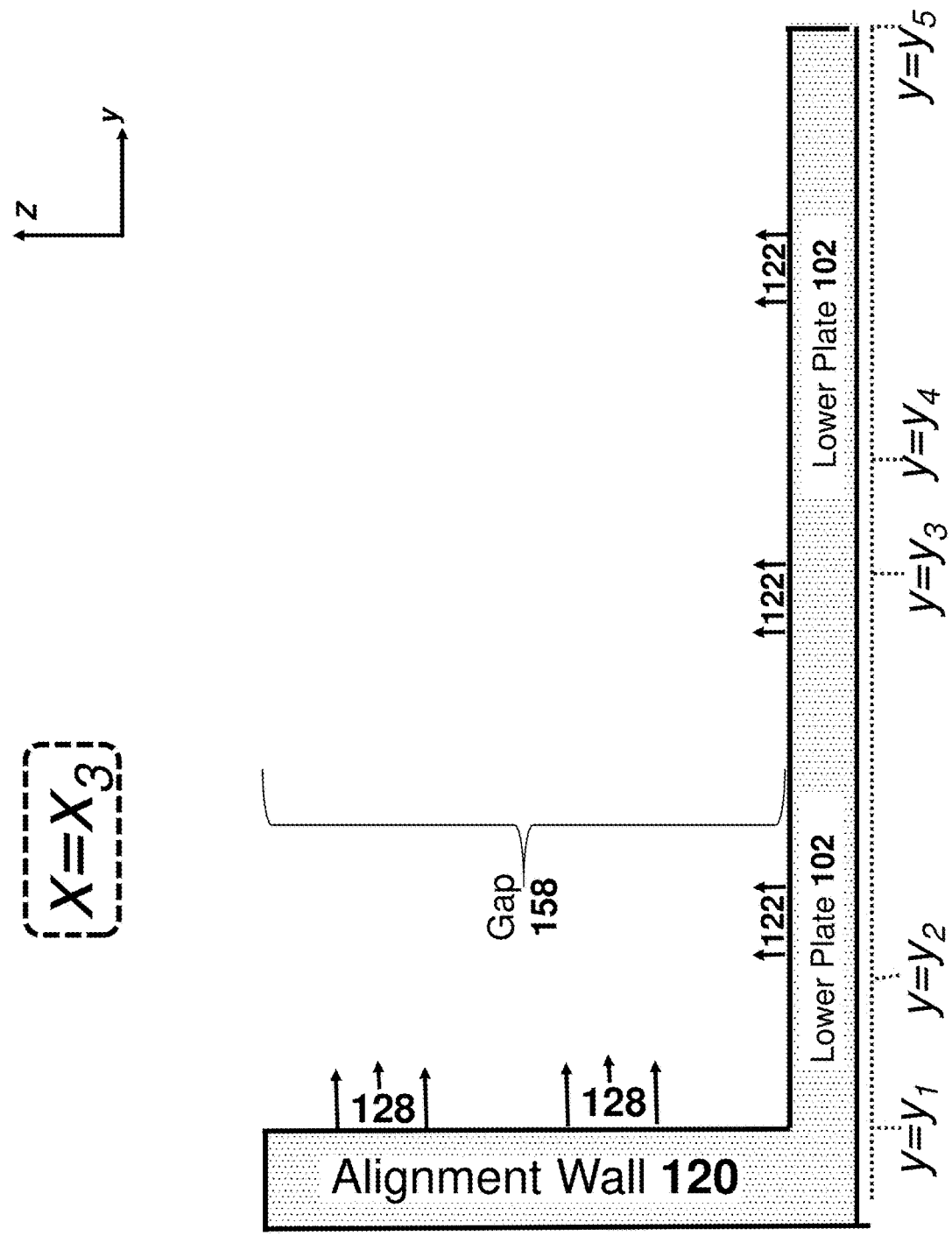
Figure 2C:
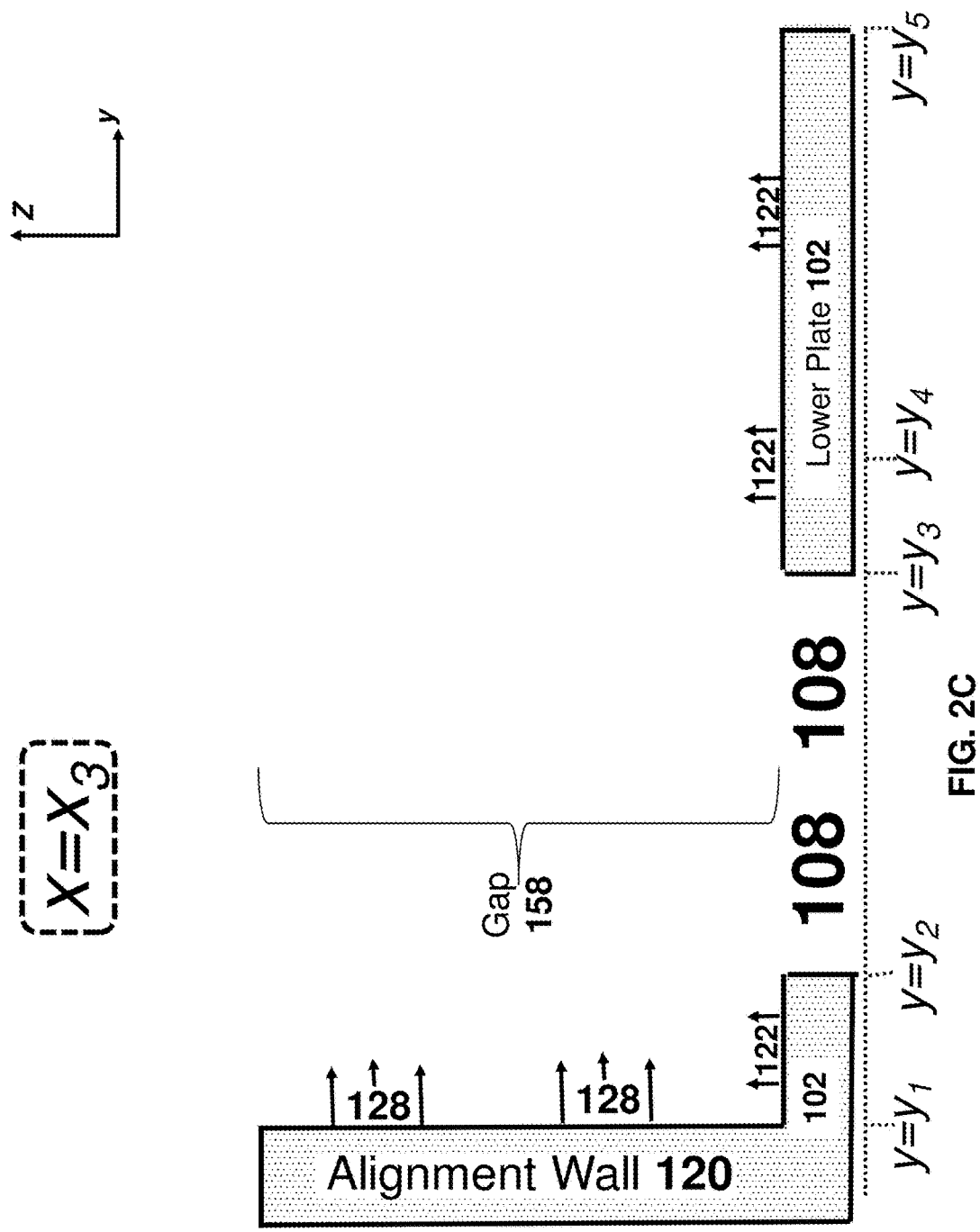
Figure 2D:
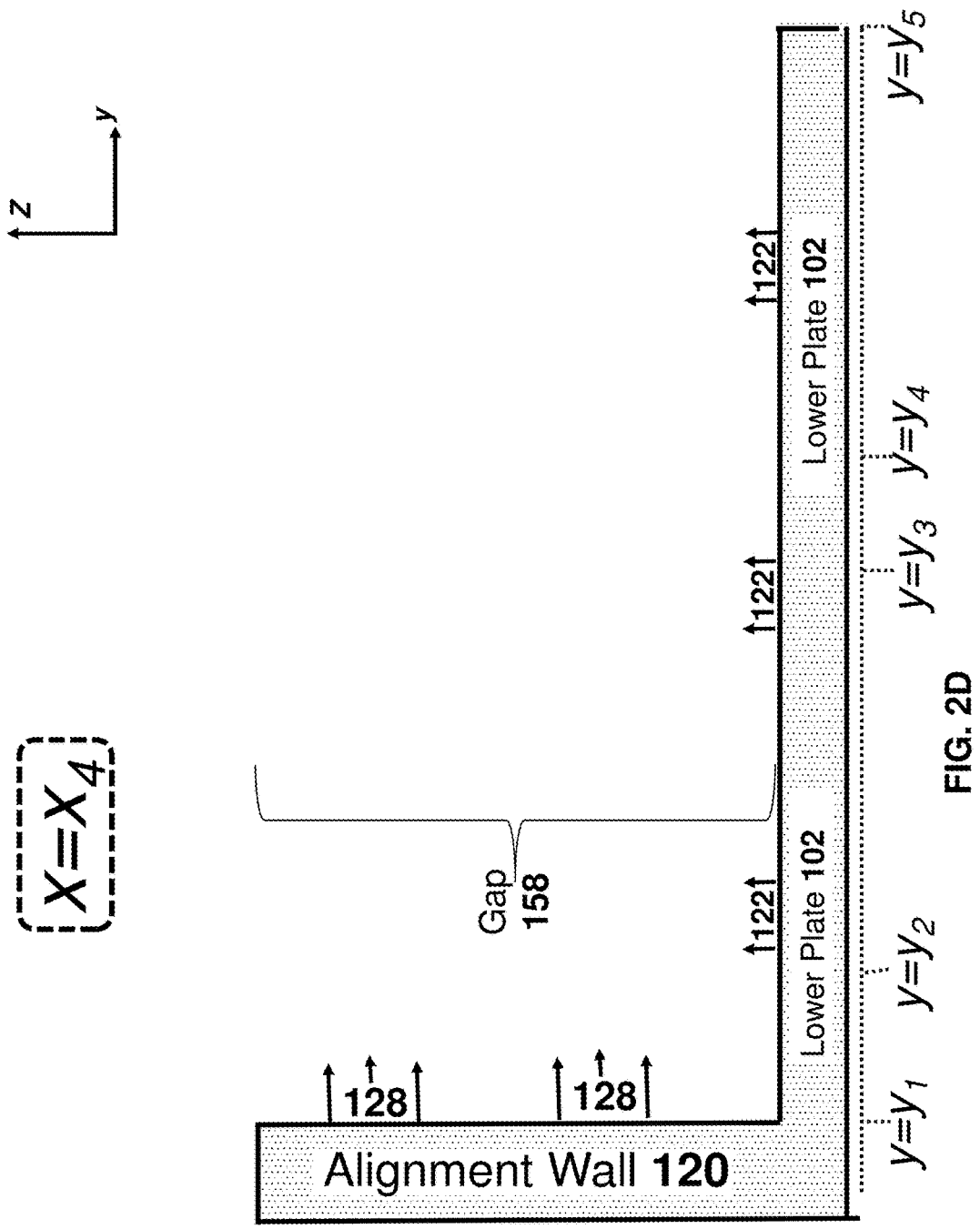
Figure 2E:
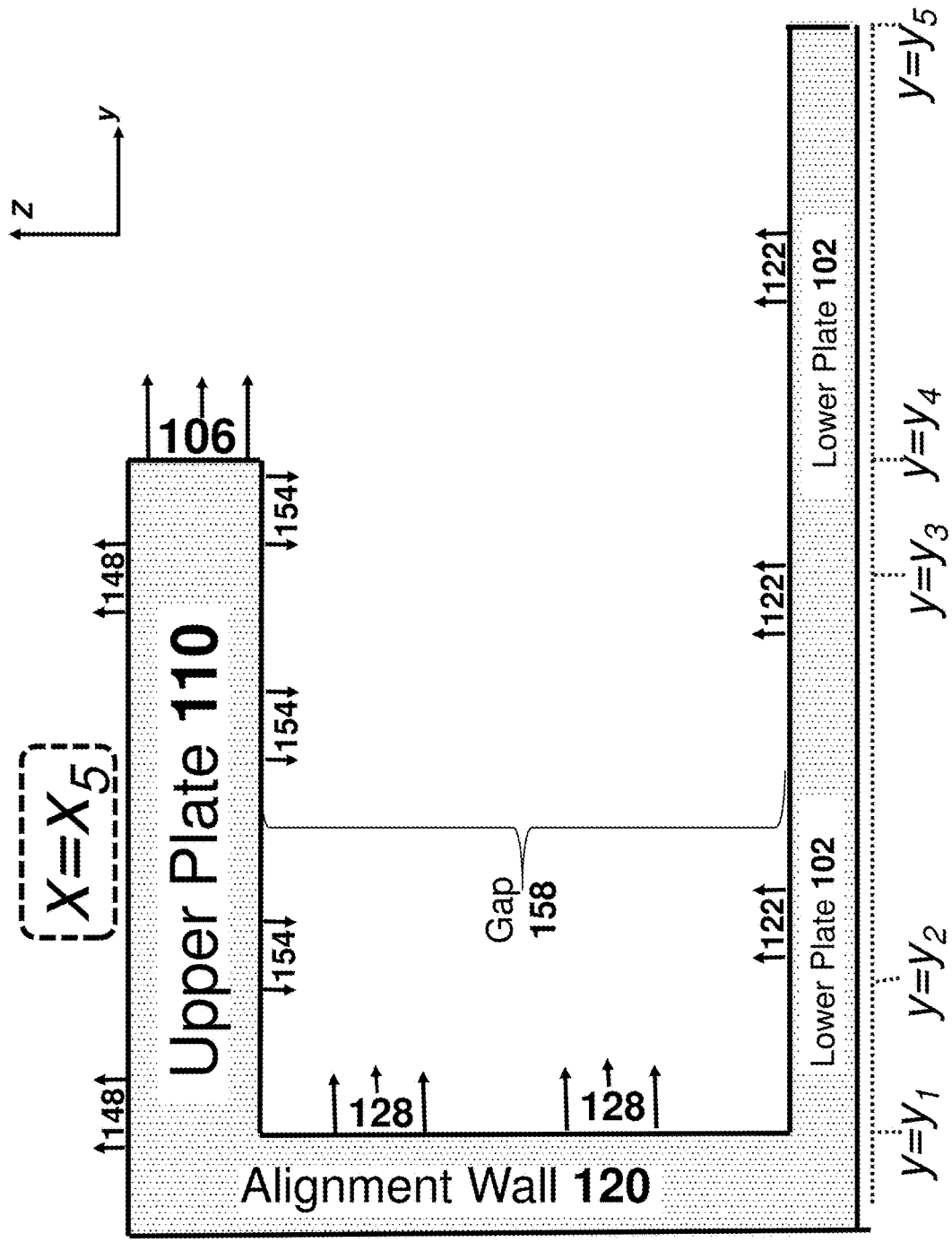

Reference is made to FIGS. 2A and 2E which are identical and respectively refer to cross sections at positions $x=x_1$, and $x=x_5$. At these x positions, hair-holder 100 comprises an open sleeve having three walls (e.g. at right-angles to each other)—upper plate 110, alignment wall 120 and lower plate 102. Furthermore, at these positions lower plate 102 extends from alignment wall 120 to a greater extent than upper plate 110. Furthermore, illustrated in FIGS. 2A and 2E as well as 1A-1B is side-facing surface 106 of upper plate 110.

Thus, as shown in FIGS. 2B and 2D, at positions $x=x_2$, and $x=x_4$ the hair-holder 100 comprises two walls—e.g. at right angles. At positions $x=x_2$, and $x=x_4$ upper-plate 110 is absent. The cross-section of FIG. 2C at position $x=x_3$ illustrates window 108 which is a void within lower plate 102.

FIGS. 3A-3E correspond to FIGS. 2A-2E—however, in the example of FIGS. 3A-3E it is shown that the hair-holder is 'flat'—i.e a characteristic length (i.e. along the x direction) and a characteristic width (i.e. along the y direction) is significantly greater (i.e. at least 3 times or at least 5 times or at least 7 times or at least 10 times) a characteristics thickness (i.e. along the z direction of the gap 158).

Figure 3A:
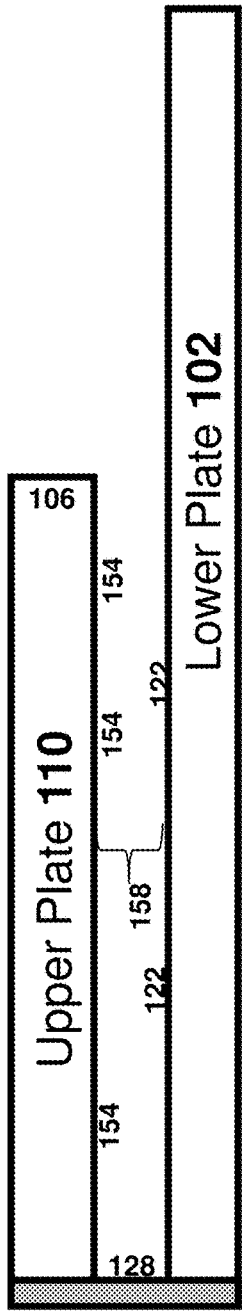
Figure 3B:
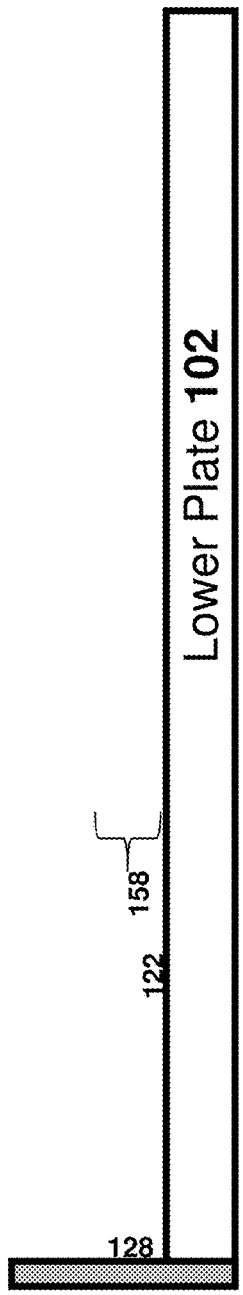
Figure 3C:
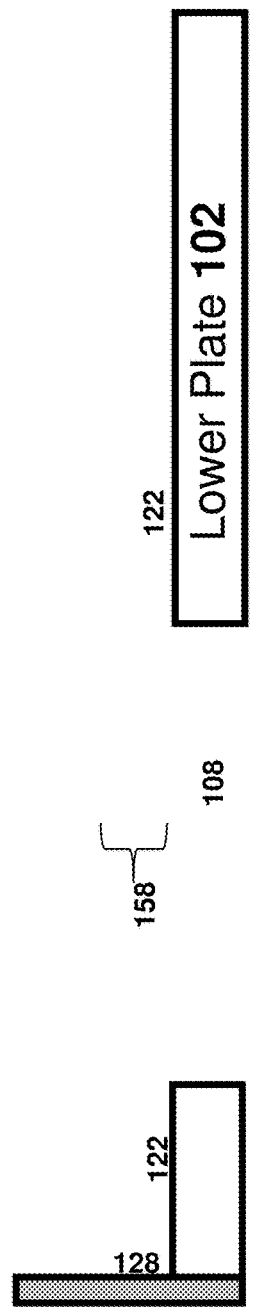

FIGS. 4A-4E illustrate the loading of hair 200 into the hair-holder of FIGS. 1-3—however, in the example of FIGS. 4A-4E of hair 200 (i.e. externally tensioned hair) (e.g. shafts of the hair sample are maintained in alignment with each other due to the external tension applied to the hair shafts) FIG. 4A corresponds to $x=x_1$ (see FIGS. 2A and 3A) and $x=x_5$ (see FIGS. 2E and 3E); FIG. 4B corresponds to $x=x_2$ (see FIGS. 2B and 3B) and $x=x_4$ (see FIGS. 2D and 3D); FIG. 4C corresponds to $x=x_3$ (see FIGS. 2C and 3C).

For each of FIGS. 4A-4E, the hair is moved while under external tension in the −y direction—'Frame A' illustrates the hair as it is being moved and some of the hair first reaches surface 106 at an earlier point in time t=t1. When a portion of the hair sample reaches and comes into contact with side-facing surface 106 of upper plate 110, the side-facing surface 106 prevents this portion from entering into the gap 158 between the upper 110 and lower 120 plate. In this manner, the presence of the upper plate 110 and side-facing surface 106 thereof regulates a 'gap distance' of gap 158—e.g. to sizes/thicknesses described above.

Not wishing to be bound by theory, it is now disclosed that (I) if this 'gap distance' is too small, then not enough hair will be present above window 108 to obtain an accurate and/or meaningful (e.g. for the purpose of predicting hair coloring) spectral and/or colorimetric measurement of hair of the sample and (ii) if this 'gap distance' is too much then 'too large of a quantity' of hair will be required to fill the hair-holder causing possible inconvenience to the hair-stylist and/of the 'subject' whose hair is being subjected to measurements.

In some embodiments, upon reaching the situation of 'frame B' static friction maintains the hair sample in an 'aligned configuration' even in the absence of external tension applied to the hair sample. Examples of this are illustrated in FIGS. 5A and 5B—in FIG. 5A external tension is still applied corresponding to FRAME "B (time=t2) for FIGS. 4A-4C while at a later time (FRAME C at time=t3) even in the absence of the external tension, the hair remains (e.g. due to static friction) in the aligned configuration within the hair-holder (e.g. at locations above window 108).

Figure 5A:
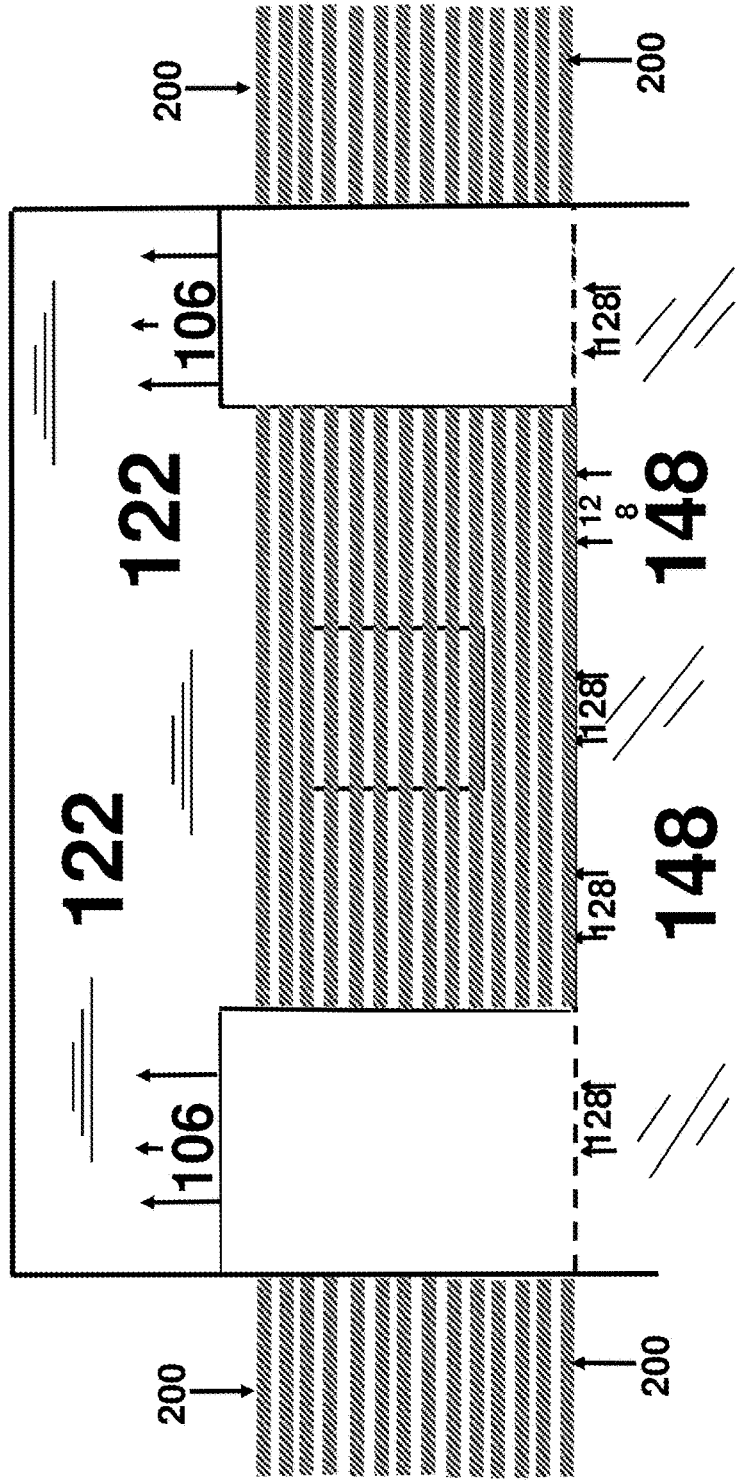
Figure 5B:
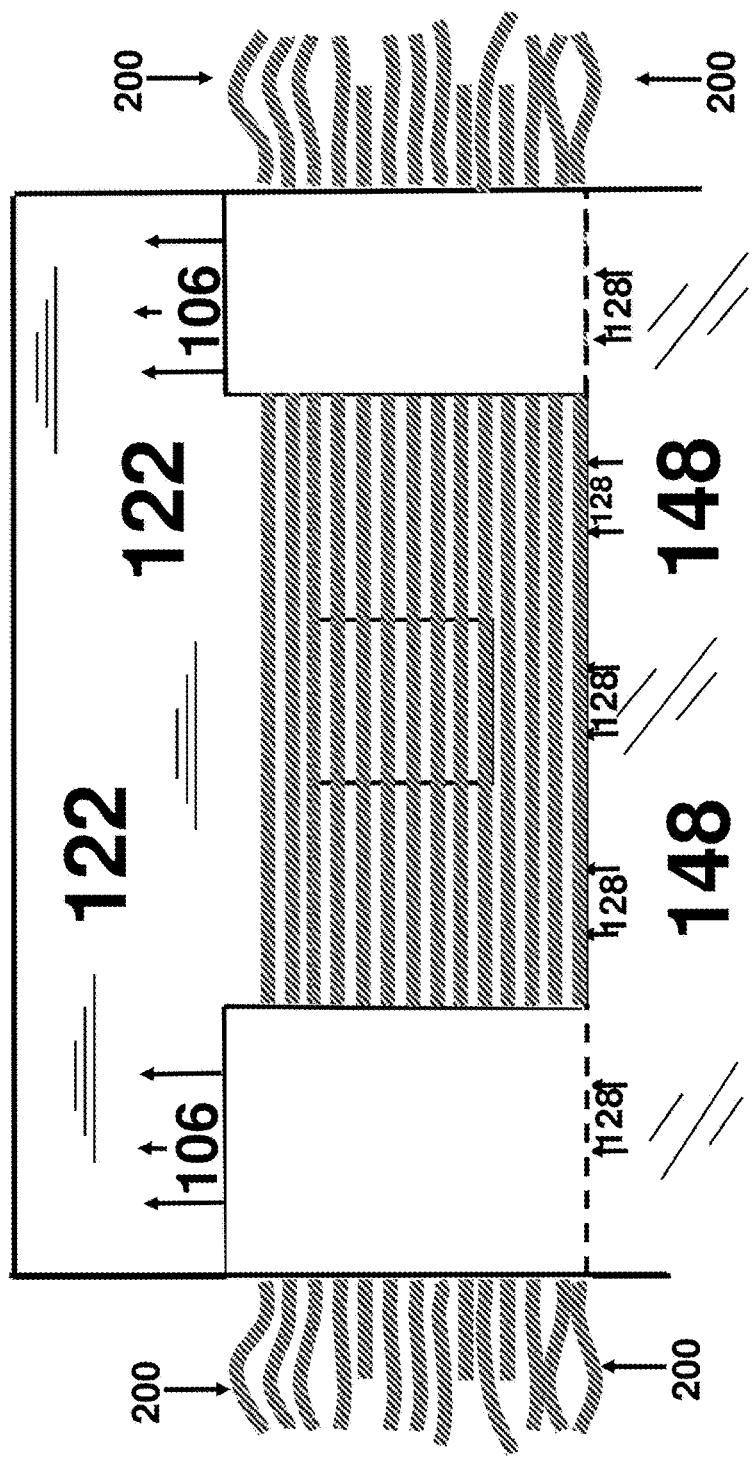

Thus, FIG. 5A is a top view of the hair-holder 100 after the hair is loaded but when the hair is under external tension. FIG. 5B is a top view of the hair-holder 100 after the hair is loaded but in the absence of external tension.

After loading, (i) the sample of hair 200 is illuminated via the window-void 108 and (ii) spectral or colorimeteric data is acquired from light that is scattered and/or deflected and/or reflected from the illuminated hair. This is shown in FIGS. 6A-6B which respectively illustrate the 'reflection configuration' and the 'transmission configuration' for the hair-holder device of FIGS. 1-5.

Figure 6A:
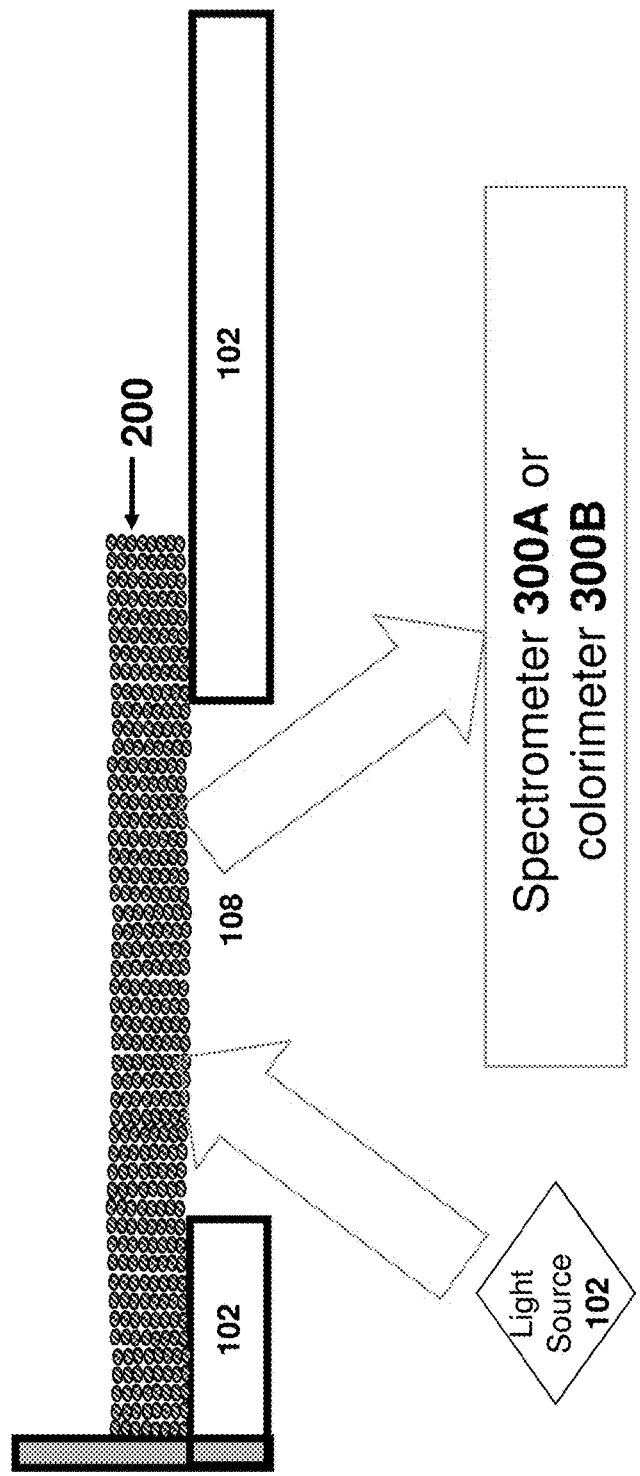

In the reflection configuration of FIG. 6A, the hair is illuminated by light source 102 (e.g. source of incoherent light) and reflected light (i.e. reflected by the illuminated hair 200) is received into spectrometer 300A or colorimeter 300B.

Figure 6B:
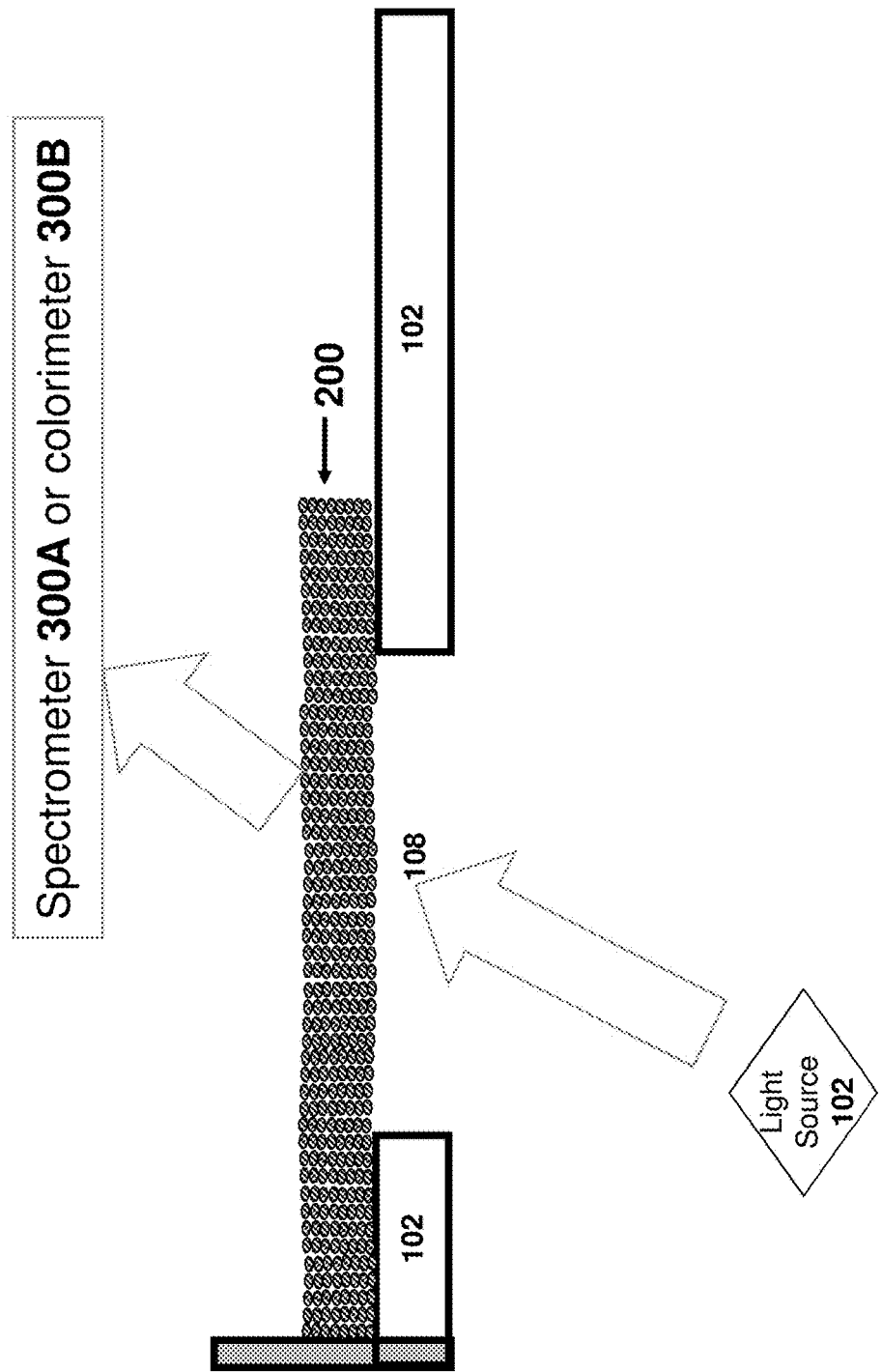

In the transmission configuration of FIG. 6B, the hair is illuminated by light source 102 (e.g. source of incoherent light) and transmitted light (i.e. transmitted by the illuminated hair 200) is received into spectrometer 300A or colorimeter 300B.

Figure 7A:
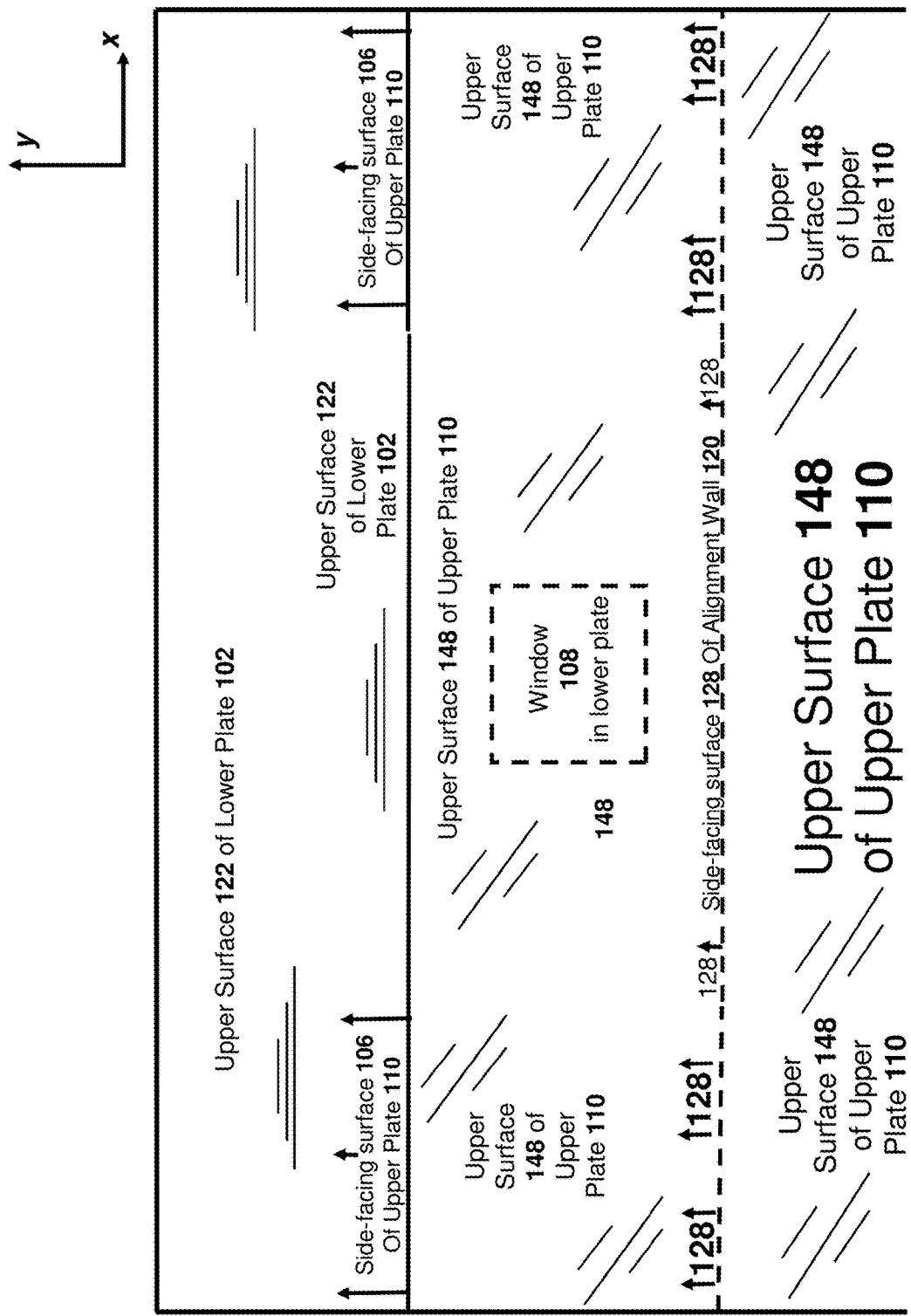
Figure 7B:
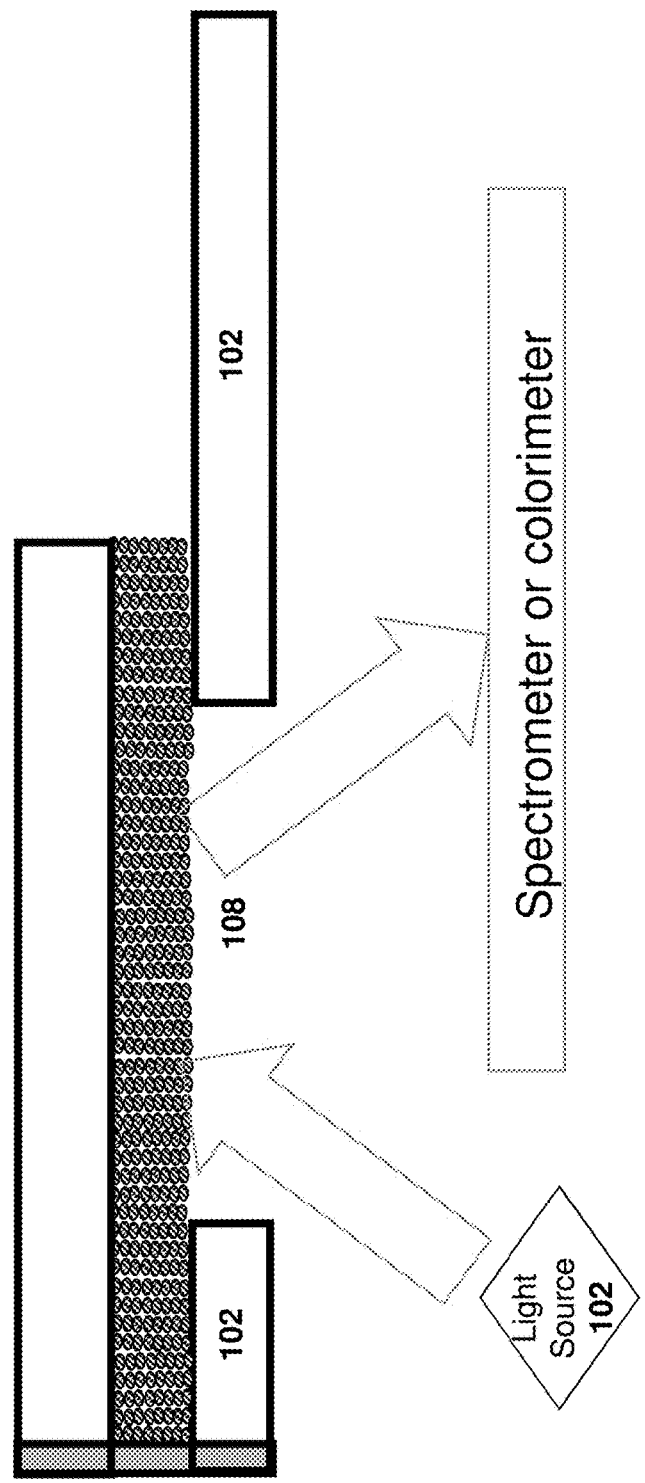

FIG. 7A illustrates an alternative hair-holder device where the 'range' of upper plate 110 is greater than for the hair-holder device of FIGS. 1-5. FIG. 7B is a side-view of the hair-holder device of FIG. 7A when used in a reflection configuration.

FIG. 8 is a side-view of a hair-holder device where the side-facing surface 128 is curved in a 'gap direction along the gap (i.e. the z direction) but is straight in a longitudinal direction (i.e. in the x direction)

Figure 9A:
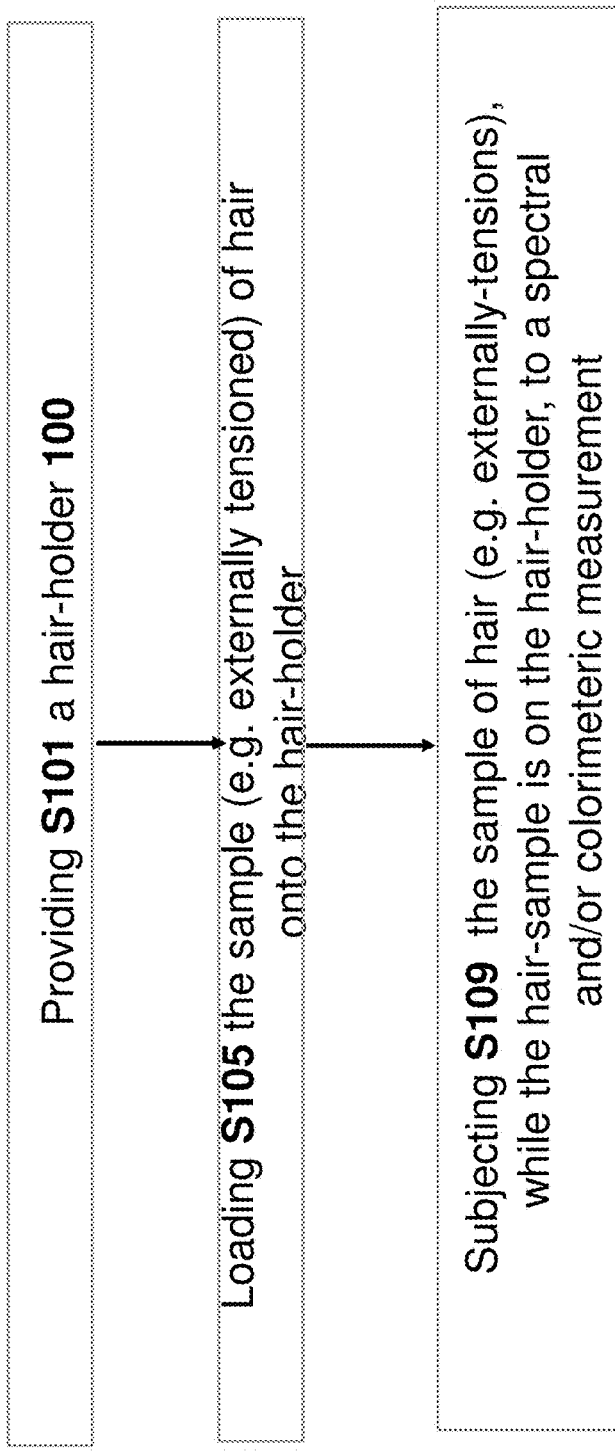
FIGS. 9A-9B illustrate a method of using the hair-holder.

FIG. 9A is a flow chart of a method of subjecting hair to a spectral and/or colorimeter measurement using a hair-holder S101. In step S101, the hair-holder 100 is provided. In step S105, a sample of hair 200 is loaded onto the hair-holder S101. In step S109, the hair is subjected to a spectral and/or colorimeteric measurement—e.g. using (i) illumination source 102 and/or (ii) spectrometer 300A or colorimeter 300B.

Figure 9B:
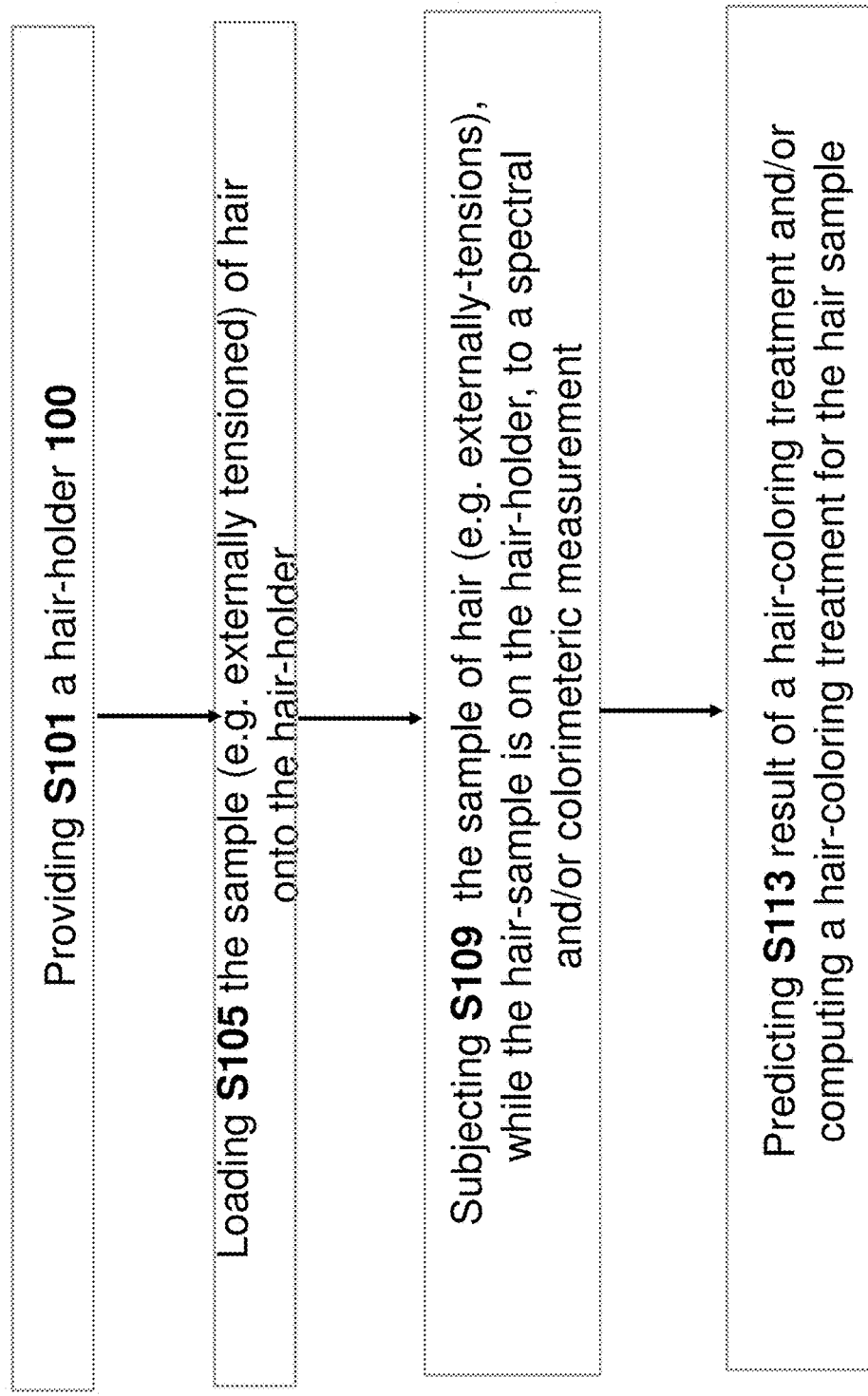

FIG. 9B is like FIG. 9A but adds the optional step of predicting S113 result of a hair-coloring treatment and/or computing a hair-coloring treatment for the hair sample. Optionally, ingredients for a hair-coloring compositions are dispensed (e.g. by an automatic mechanized dispenser in response and in accordance with the spectra or colorimetric data of the hair 200 is measured in step S109.

Some of these steps will now be discussed, in accordance with example embodiments.

Step S101

In some embodiments, hair-holder 100 comprises: i. upper 110 and lower 102 plate assemblies respectively having downward-facing 154 and upward-facing 122 opposing surfaces defining a fixed gap 158 therebetween, a height of the fixed-gap 158 ranging between at least 200 microns (e.g. at most 300 microns or at most 400 microns or at most 500 microns) and at most 1 cm (e.g. at most 5 mm or at most 3 mm or at most 2 mm or at most 1.5 mm or at most 1 mm), the upper plate 110 assembly further comprising a sideward-facing sample-thickness-regulating surface 106 above the fixed-gap.

In some embodiments, hair-holder 100 further comprises: ii. an alignment-wall 120 directly or indirectly rigidly attached to both 110, 102 plate assemblies, the alignment-wall 120 having a side-facing alignment surface 128 within gap 158 or sideways-facing into the gap 158, the alignment surface 128 being straight along a longitudinal direction parallel to both 154, 122 of the opposing surfaces.

In some embodiments, hair-holder 100 further comprises: a window-void 108 coplanar and/or within the upward-facing 122 surface.

In some embodiments, at both first (e.g. when $x=x_1$—see FIG. 2A) and second (e.g. when $x=x_5$—see FIG. 2E) locations along the longitudinal direction (e.g. the alignment direction of hair of the hair sample), a cross-section of the hair-holder 100 is that of a 3-sided sleeve facing away from the alignment wall 120 such that the lower support surface 122 extends further away from the alignment wall 100 than the upper support surface. For example, the first and second locations may be disposed at opposite longitudinal sides of the window-void 108.

In some embodiments, hair-holder device 100 of any the figures is 'flat'—i.e. a ratio between (i) a distance between a centroid of window-void 108 and alignment-wall 120 (or surface 128 thereof) and (ii) a thickness of gap 158 (or a representative thickness of the hair-sample of over window-void 108) is at least 3 or at least 5 or at least 10.

Step S105

In step S105, the sample of hair 200 (e.g. under externally-tension—i.e. sufficient external tension to maintain shafts of the hair-sampled aligned with each other to design a longitudinal and/or alignment direction—e.g. aligned in the x-direction) is loaded onto hair holder 100. The loading may be formed by laterally (i.e. in the y-direction—i.e. in a direction perpendicular to alignment surface 128) moving shafts of the sample of hair 200 towards the alignment surface 128.

In different embodiments, this may be performed such that during loading, a presence of the sideward-facing sample-thickness-regulating surface 106 on opposite longitudinal-sides of the window-void 108 (e.g. at $x=x_1$ and $x=x_5$) regulates an amount of hair permitted to enter the gap so as to regulate a thickness of hair above the window-void 108. This thickness may be regulated to at least 200 microns (e.g. at most 300 microns or at most 400 microns or at most 500 microns) and/or at most 1 cm (e.g. at most 5 mm or at most 3 mm or at most 2 mm or at most 1.5 mm or at most 1 mm).

In some embodiments, after loading and after release of the external tension (i.e. so the hair is no longer externally tensioned—e.g. so no tension is applied on the hair and the only relevant forces applied upon hair above the window 108 are applied by hair holder 100), static friction applied by the side-facing alignment surface 128 upon shafts of the hair sample maintain alignment of hair above the window-void 108;

Step S109

In step S105, the sample of hair 200 is subjected to a spectral and/or colorimeteric measurement by illuminating the hair via the window-void.

Step S113

As noted above, the spectral or colorimeteric data is analyzed in order to (i) predict the outcome of a hypothetical hair-coloring treatment as applied to the hair and/or (ii) calculate a customized hair-coloring treatment for the hair.

Figure 10:
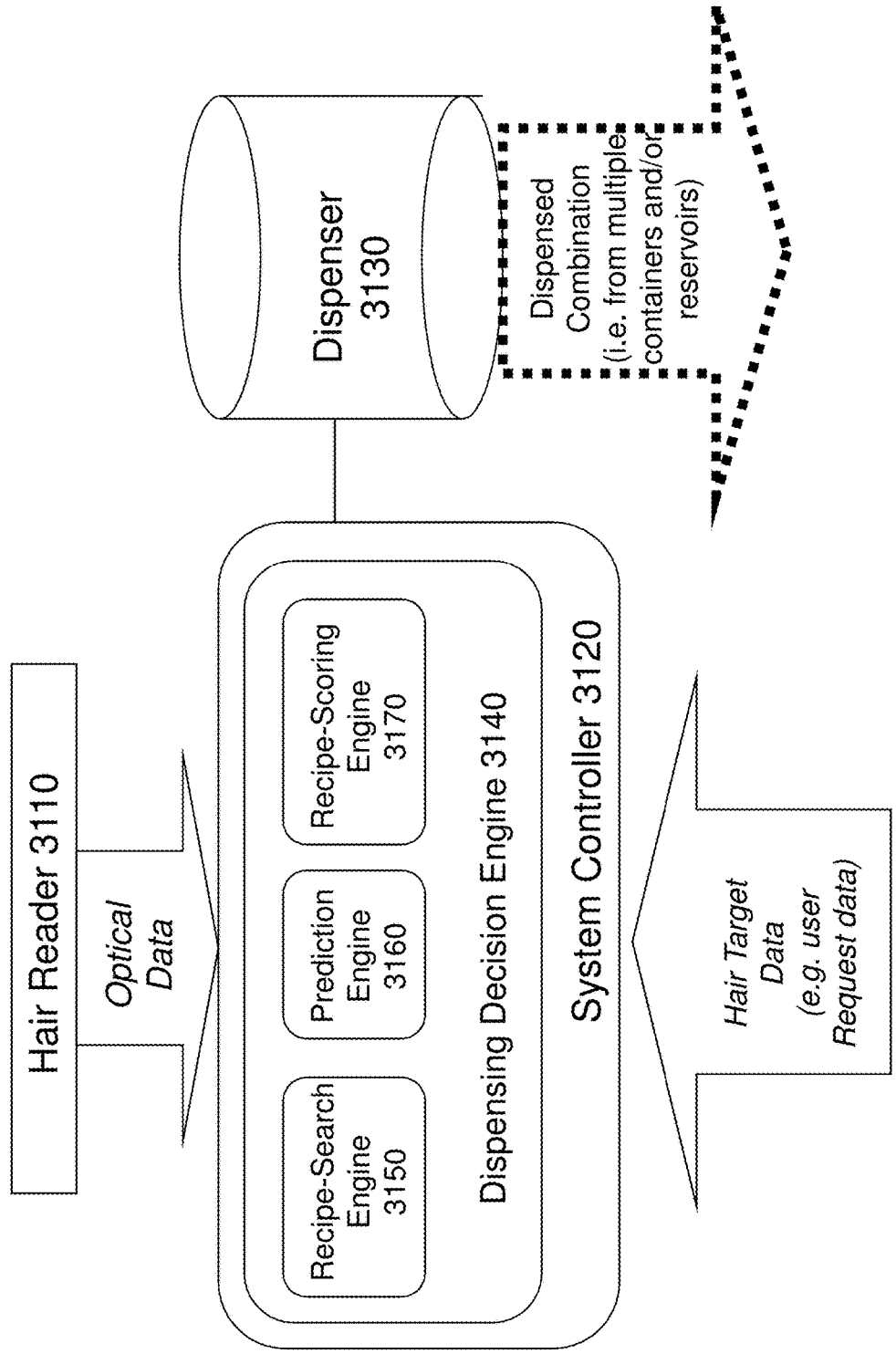
FIG. 10 is a flow-chart off a system including the hair-holder.

FIG. 10 is a block diagram of a system for (i) optically measuring one or properties (e.g. spectra or colorimetric data) of hair and, (ii) in accordance with the optically-measured properties, dispensing material from containers to provide a customized hair-coloring composition. For example, a user desires to color his/her hair to a target shade. An optical measurement of the user's "initial hair" is performed, and a hair-coloring composition, customized according to the initial state of the user's hair as well as the hair-coloring target is prepared.

Illustrated in FIG. 10 are hair reader 3110 (e.g. comprising hair-holder 100 and a colorimeter and/or spectrometer), system controller 3120, and dispenser device 3130. In the non-limiting example of FIG. 9, system controller 3120 includes dispensing decision engine 3140 which includes recipe-search engine 3150, prediction engine 3160 and recipe-scoring engine 3170.

Hair reader 3110 optically acquires optical data from hair—for example by illuminating the hair and detecting light reflected by and/or transmitted by and/or deflected by the hair. System controller 3120 (e.g. comprising a digital computer) receives both the optical data and hair target data (e.g. describing a target shade desired the user). In accordance with the received data, the system controller 3120 computes (e.g. dispensing decision engine 3140) using a customized recipe for the hair-coloring composition—e.g. including respective quantities of a plurality of different materials stored in dispenser 3110.

The dispenser proceeds to dispense the materials for the hair-coloring composition. These materials may be automatically or manually mixed to form a customized hair-coloring composition, which is applied to the user's hair.

FIG. 11

Figure 11:
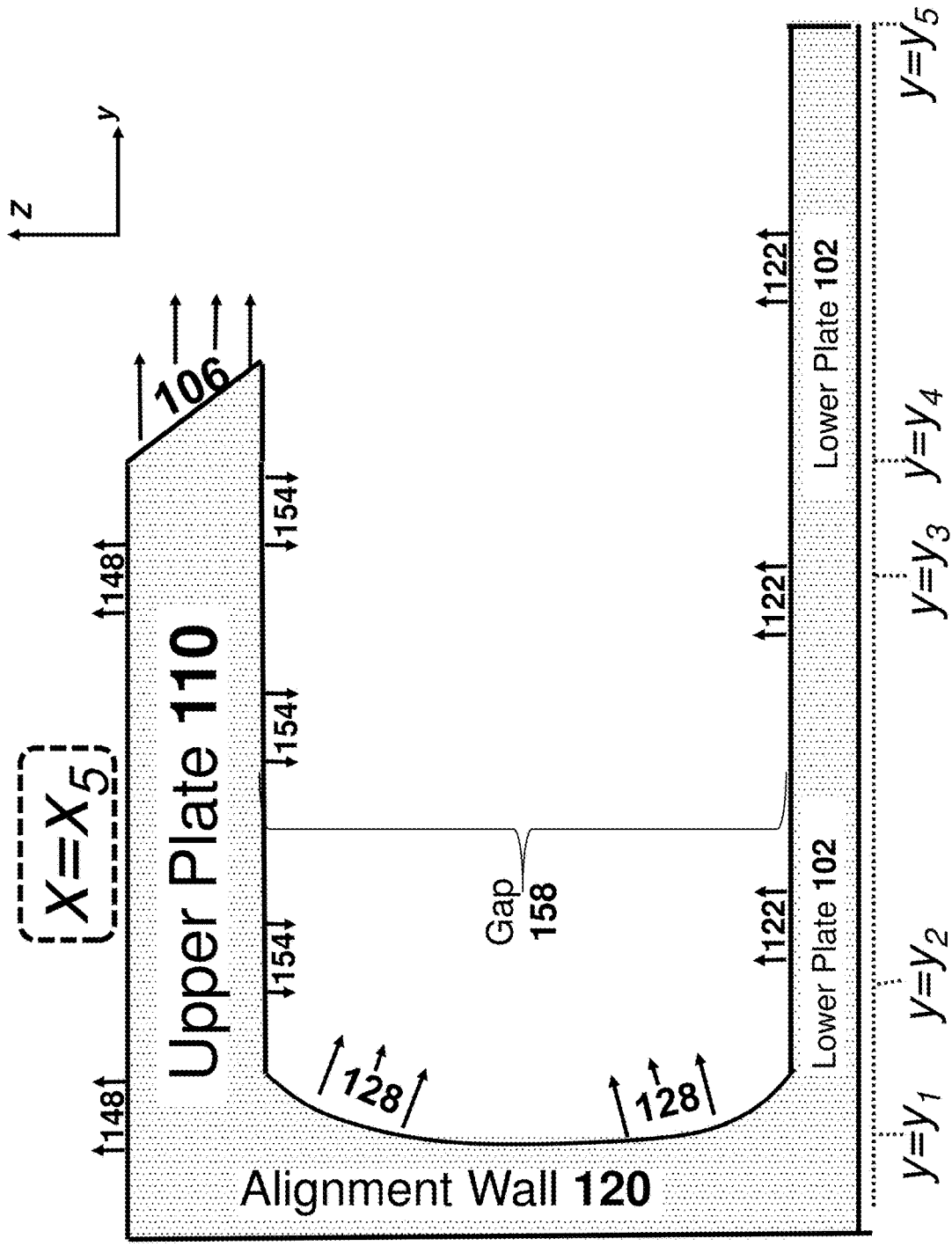

As shown in FIG. 11, surface 106 is not required to be straight.

FIGS. 12A-12C

Figure 12A:
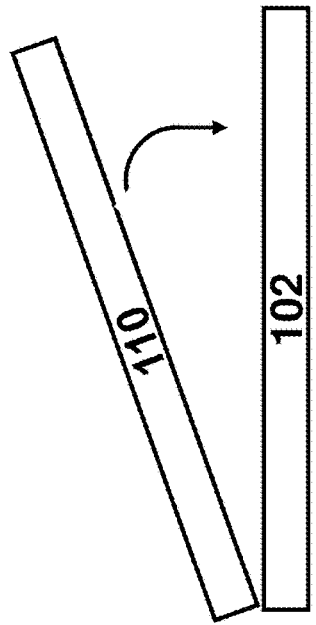
FIG. 12A-12C illustrate assembly of the hair-holder by rotation.
Figure 12B:
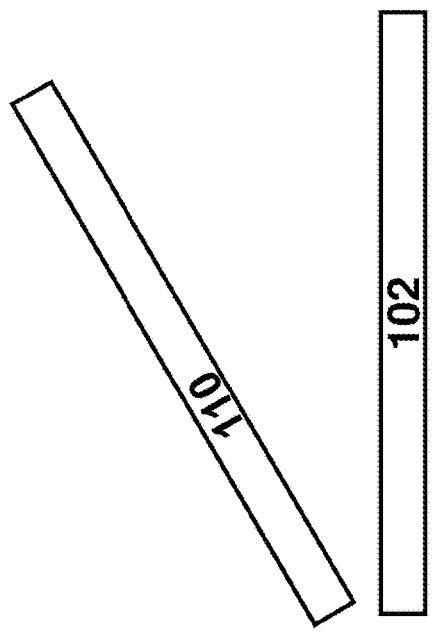
Figure 12C:
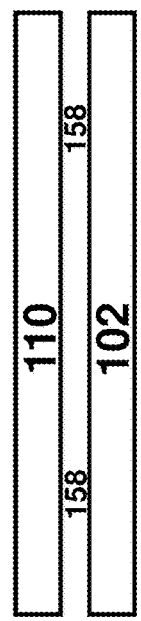

FIGS. 12A-12C show one non-limiting method of assembling the hair-holder by rotation of one plate assembly relative to the other plate assembly.

Concluding Remarks

Some embodiments of the present invention relate to methods and apparatus that were disclosed in PCT/IB2012/051351 which (i) was filed on Mar. 21, 2012; (ii) was published as WO/2012/127429; and (iii) is incorporated herein by reference in its entirety. In some embodiments, any feature or combination of features described in the present document may be combined with any feature of combination of features described in application PCT/IB2012/051351.

Some embodiments of the present invention relate to methods and apparatus that were disclosed in PCT/IL2014/050850 which (i) was filed on Sep. 28, 2014; (ii) was published as WO/2015/044944; and (iii) is incorporated herein by reference in its entirety. In some embodiments, any feature or combination of features described in the present document may be combined with any feature of combination of features described in application PCT/IL2014/050850.

Some embodiments of the present invention relate to methods and apparatus that were disclosed in PCT/IB2015/000724 which (i) was filed on Mar. 25, 2015; (ii) was published as WO/2015/166340; and (iii) is incorporated herein by reference in its entirety. In some embodiments, any feature or combination of features described in the present document may be combined with any feature of combination of features described in application PCT/IB2015/000724.

Some embodiments of the present invention relate to methods and apparatus that were disclosed in PCT/IB2015/053065 which (i) was filed on Apr. 27, 2015; (ii) was published as WO/2015/166403; and (iii) is incorporated herein by reference in its entirety. In some embodiments, any feature or combination of features described in the present document may be combined with any feature of combination of features described in application PCT/IB2015/053065.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for optically acquiring data from hair, the system comprising:
   a hair-holder including:
      upper and lower plate assemblies respectively having downward-facing and upward-facing opposing surfaces defining a gap therebetween, the lower plate assembly having a window-void therein, the upper plate assembly further comprising a sideward-facing sample-thickness-regulating surface above the gap; and
      an alignment-wall mechanically coupled to both plate assemblies and having a side-facing alignment surface: within gap or sideward-facing into the gap, the alignment surface being straight along a longitudinal direction parallel to both of the opposing surfaces,
   the hair-holder being configured so that:
      When an externally-tensioned sample of hair is loaded onto the hair-holder by laterally moving the sample towards the alignment surface, a presence of the sideward-facing sample-thickness-regulating surface regulates an amount of hair permitted to enter the gap, thereby regulating a thickness of hair above the window-void to at least 0.5 mm and at most 2 mm; and
      after the loading and after release of the external tension, static friction applied by the side-facing alignment surface upon shafts of the hair sample maintain alignment of hair above the window-void.

2. The system of claim 1 further comprising at least one light-source configured to illuminate the aligned shafts via the window-void.

3. The system of claim 2 wherein the light-source is selected from the group consisting of an LED, a halogen source and a high intensity discharge source.

4. The system of claim 2 wherein the light-source emits light at a wavelength of at least 750 nm.

5. The system of claim 1 further comprising a spectrometer for measuring at least one spectrum of the aligned shafts upon receiving, via the window-void, light reflected by or transmitted by or deflected by the aligned shafts.

6. The system of claim 1 further comprising a digital camera for digitally acquiring a digital image of the aligned shafts upon receiving, via the window-void, from light reflected by or transmitted by or deflected by the aligned shafts.

7. The system of claim 6 further comprising a hair-coloring prediction engine for predicting from the digital image and/or from a spectrum of the aligned shafts measured by a spectrometer, a result of a hypothetical hair-coloring treatment upon hair of the sample.

8. The system of claim 7 further comprising an automatic dispenser having a plurality of compartments, each compartment storing a different respective hair-coloring material, the dispenser configured to produce a mixture of ingredients for a customized hair-coloring treatment by automatically dispensing material from each of the compartments at relative quantities computed in accordance with the digital image or the spectrum or the prediction of the hair-coloring treatment.

9. The system of claim 1, where the upper plate assembly has a window-void therein, at least a portion of the window-void of the upper plate assembly being directly above the window-void of the lower plate assembly.

10. A method for optically acquiring data from hair, the method comprising:
   providing a hair-holder including:
      upper and lower plate assemblies respectively having downward-facing and upward-facing opposing surfaces defining a fixed gap therebetween defining a gap therebetween, the lower plate assembly having a window-void therein, the upper plate assembly further comprising a sideward-facing sample-thickness-regulating surface above the gap; and
      an alignment-wall mechanically coupled to both plate assemblies and having a side-facing alignment surface within gap or sideward-facing into the gap, the alignment surface being straight along a longitudinal direction parallel to both of the opposing surfaces;
   receiving an externally-tensioned sample of hair onto the hair-holder such that the externally-tensioned sample of hair is laterally moved towards the alignment surface and a presence of the sideward-facing sample-thickness-regulating surface regulates an amount of hair permitted to enter the gap, thereby regulating a thickness of hair above the window-void to a fixed value of at least 0.5 mm and at most 2mm; and
   after the loading and after release of the external tension, the side-facing alignment surface applies static friction upon shafts of the hair sample so as to maintain alignment of hair above the window-void.

11. The method of claim 10 further comprising illuminate the aligned shafts via the window-void.

12. The method of claim 11 wherein the light-source is selected from the group consisting of an LED, a halogen source and a high intensity discharge source.

13. The method of claim 11 wherein the light-source emits light at a wavelength of at least 750 nm.

14. The method of claim 10 further comprising receiving, via the window-void and by a spectrometer, light that is reflected by or transmitted by or deflected by the aligned shafts, so as to measure at least one spectrum of the aligned shafts.

15. The method of claim 10 further comprising receiving, via the window-void and by a digital camera, light that is reflected by or transmitted by or deflected by the aligned shafts, so as to digitally acquire an image of the aligned shafts.

16. The method of claim 15 further comprising electronically operating a hair-coloring prediction engine to predict from the digital image and/or from a spectrum of the aligned shafts measured by a spectrometer, a result of a hypothetical hair-coloring treatment upon hair of the sample.

17. The method of claim 16 further comprising:
   providing an automatic dispenser having a plurality of compartments, each compartment storing a different respective hair-coloring material; and operating the automatic dispenser to produce a mixture of ingredients for a customized hair-coloring treatment by automatically and electronically dispensing material from each of the compartments at relative quantities computed in accordance with the digital image or the spectrum or the prediction of the hair-coloring treatment.

* * * * *